(12) United States Patent
Segal et al.

(10) Patent No.: US 6,300,141 B1
(45) Date of Patent: Oct. 9, 2001

(54) CARD-BASED BIOSENSOR DEVICE

(75) Inventors: Donald Segal, Stouffville; Heman Chao; Wah Y. Wong, both of Edmonton; Jerry McElroy, Richmond Hill, all of (CA)

(73) Assignee: Helix BioPharma Corporation, Aurora (CA)

( * ) Notice: Subject to any disclaimer, the term of this patent is extended or adjusted under 35 U.S.C. 154(b) by 0 days.

(21) Appl. No.: 09/518,178

(22) Filed: Mar. 2, 2000

Related U.S. Application Data

(60) Provisional application No. 60/122,546, filed on Mar. 2, 1999.

(51) Int. Cl.[7] .................. G01N 33/543; G01N 27/26; G01N 33/00; C12M 1/34; C25D 21/12

(52) U.S. Cl. ................. 436/518; 436/86; 436/164; 436/524; 436/527; 436/536; 435/4; 435/6; 435/7.1; 435/7.5; 435/7.92; 435/7.93; 435/174; 435/176; 435/287.1; 435/287.2; 435/28.87; 204/228.1; 204/229.8; 204/230.2; 204/400; 204/403; 204/406; 204/407; 204/409; 204/422; 349/1; 349/2; 349/33; 422/68.1

(58) Field of Search .................. 204/228.1, 229.8, 204/230.2, 400, 403, 406, 407, 409, 422; 349/1, 2, 33; 435/4, 6, 7.1, 7.5, 7.92–7.93, 174, 176, 287.1, 287.2, 288.7; 436/86, 164, 518, 524, 527, 536; 422/68.1

(56) References Cited

U.S. PATENT DOCUMENTS

| | | | |
|---|---|---|---|
| 5,200,051 | * | 4/1993 | Cozzette et al. .............. 204/403 |
| 5,246,846 | * | 9/1993 | Pittner et al. ............... 435/174 |
| 5,405,783 | * | 4/1995 | Pirrung et al. ............... 436/518 |

(List continued on next page.)

FOREIGN PATENT DOCUMENTS

| | | | |
|---|---|---|---|
| 0 505 494 B1 | * | 9/1992 | (EP). |
| WO 97/41424 | * | 11/1997 | (WO). |

OTHER PUBLICATIONS

Chao et al. Use of heterodimeric coiled–coil system for biosensor application and affinity purification. J. Chromatography. (1998)vol. 715, pp. 307–329.*

Primary Examiner—Christopher L. Chin
Assistant Examiner—Kartic Padmanabhan
(74) Attorney, Agent, or Firm—Peter J. Dehlinger

(57) ABSTRACT

A diagnostic card device for use in detecting or quantitating an analyte present in a liquid sample, comprising a card substrate having a sample introduction region, a biosensor, and a sample-flow pathway communicating between the sample-introduction region and the biosensor, circuitry for generating an analyte-dependent electrical signal from the biosensor; and a signal-responsive element for recording such signal. In one biosensor, the biosensor includes a detection surface with surface-bound molecules of a first charged, coil-forming peptide capable of interacting with a second, oppositely charged coil-forming peptide to form a stable α-helical coiled-coil heterodimer, where the binding of the second peptide to the first peptide, to form such heterodimer, is effective to measurably alter a signal generated by the biosensor. The sample-flow pathway contains diffusibly bound conjugate of the second coil-forming peptide and the analyte (or an analyte analog) and immobilized analyte-binding agent. The analyte in the liquid sample and the conjugate compete for binding with the immobilized analyte-binding agent. Unbound conjugate migrates by capillarity to the biosensor. Liquid sample containing conjugate migrates in the sample flow pathway by capillary action or is driven by a micro-pump. In another embodiment, the biosensor includes an electrode substrate coated with a high-dielectric hydrocarbon-chain monolayer, and having analyte-binding agent attached to the exposed monolayer surface. Binding of analyte to the monolayer-bound analyte-binding agent, and the resultant perturbation of the monolayer structure, causes ion-mediated electron flow across the monolayer.

16 Claims, 26 Drawing Sheets

U.S. PATENT DOCUMENTS

| | | | |
|---|---|---|---|
| 5,436,170 | * | 7/1995 | Cornell et al. ........................ 436/527 |
| 5,580,794 | * | 12/1996 | Allen .................................... 436/169 |
| 5,624,537 | * | 4/1997 | Turner et al. ........................ 204/403 |
| 5,723,345 | * | 3/1998 | Yamauchi et al. ................... 436/518 |
| 5,736,410 | * | 4/1998 | Zarling et al. ....................... 436/172 |
| 5,942,388 | * | 8/1999 | Willner et al. ........................... 435/6 |
| 5,955,379 | * | 9/1999 | Lennox et al. ........................ 436/528 |
| 6,069,825 | * | 8/2000 | Garnier ................................ 525/54.1 |
| 6,074,616 | * | 6/2000 | Buechler et al. .................... 422/104 |
| 6,107,080 | * | 8/2000 | Lennox ............................. 435/283.1 |
| 6,165,335 | * | 12/2000 | Lennox et al. ........................ 204/403 |

\* cited by examiner

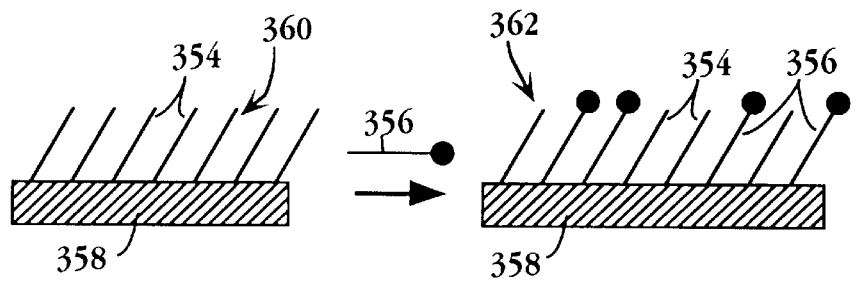
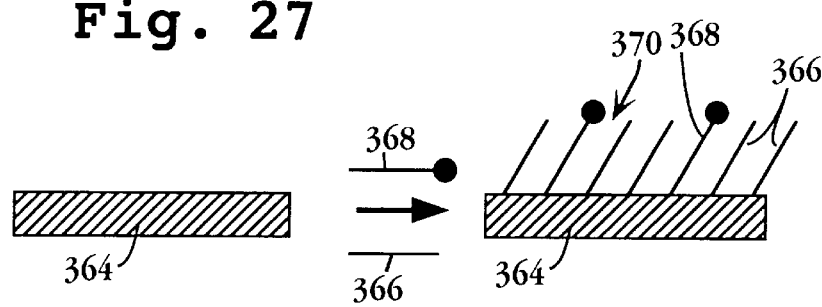
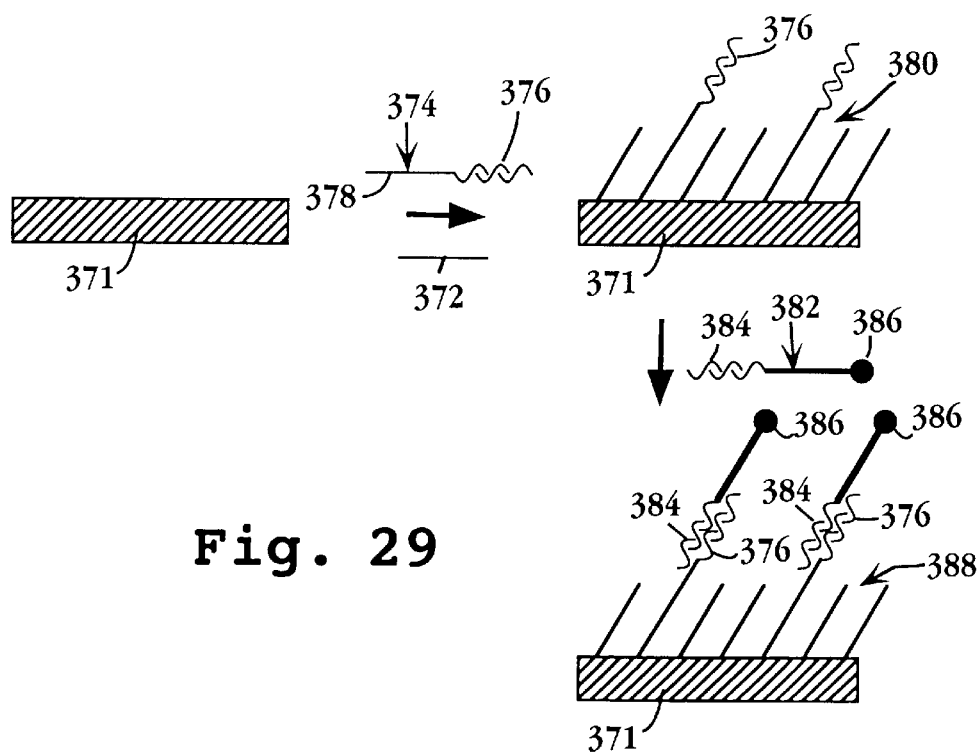

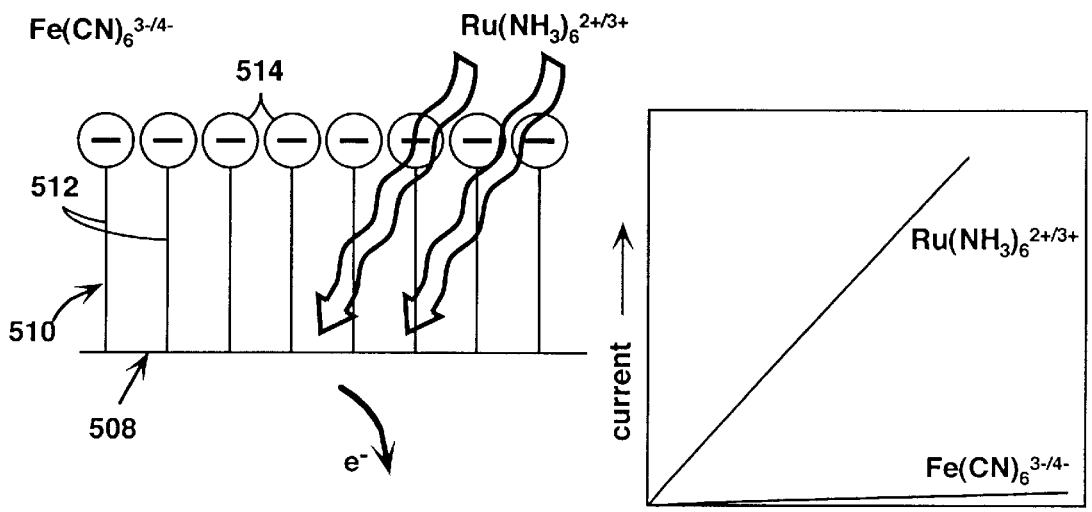
Fig. 40
Fig. 41
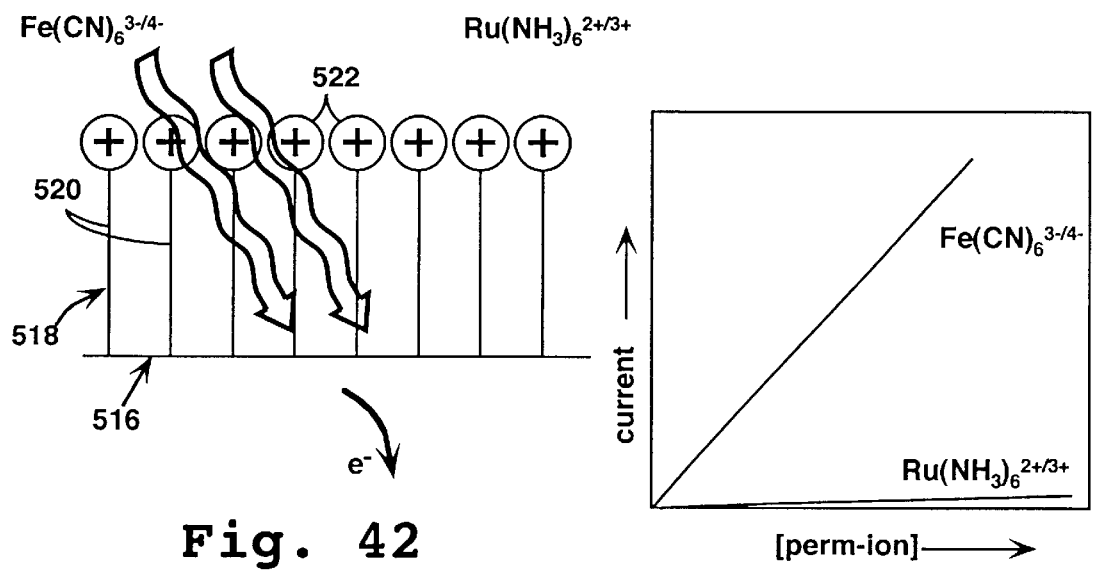
Fig. 42
Fig. 43

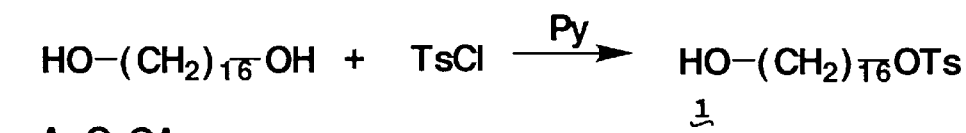
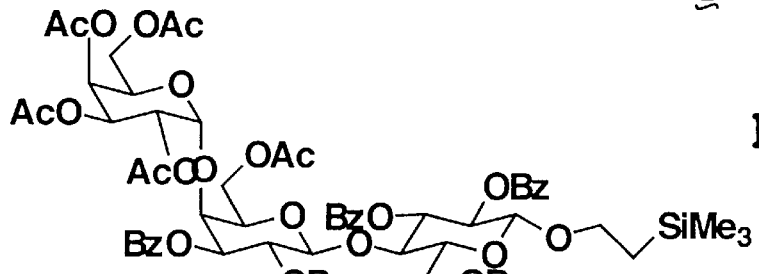
Fig. 49
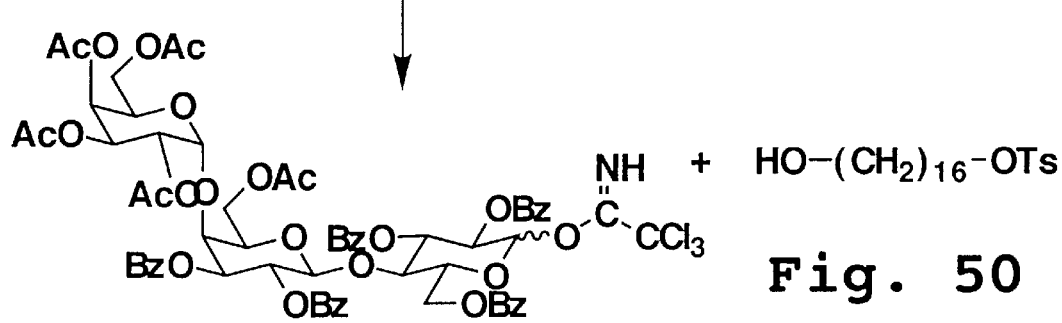
Fig. 50
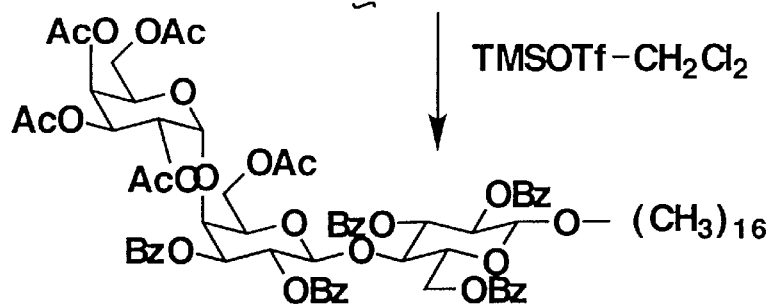
Fig. 51
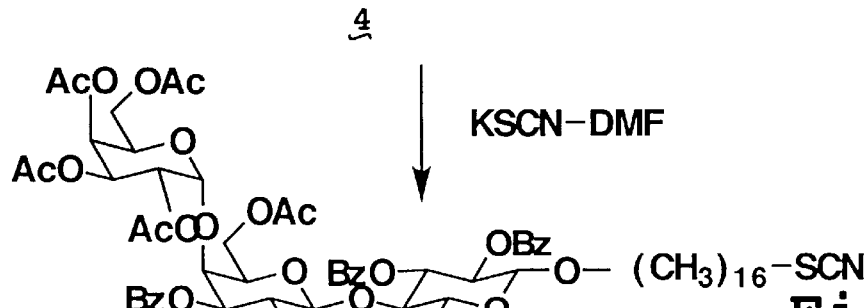
Fig. 52

CARD-BASED BIOSENSOR DEVICE

This application claims priority to U.S. Provisional Patent Application No. 60/122,546 filed Mar. 2, 1999, now pending, which is incorporated herein by reference.

FIELD OF THE INVENTION

In general, the invention relates to test cards which incorporate biosensor detectors. In particular, the invention relates to a disposable self-contained, electronic assay device incorporating a biosensor which is based on the binding of an analyte with an analyte-binding agent.

BACKGROUND OF THE INVENTION

The development of a rapid, simple method for carrying out a range of biochemical assays would greatly enhance the field of diagnostics, particularly in areas such as the health care, environmental monitoring and food industries. For effective "on-site" use, the device should be operated with the minimum amount of manual manipulation and be suitable for use by non-specialists operators. Self-contained disposable test cards utilizing liquid flow channels are a convenient and economical assay platform and are used for detecting or quantitating biological analytes based on analyte-specific binding between an analyte and an analyte-binding receptor or agent. Analyte/analyte binding pairs encountered commonly in diagnostics include antigen-antibody, hormone-receptor, drug-receptor, cell surface antigen-lectin, biotin-avidin, and complementary nucleic acid strands. The advantages of a card format include convenience, privacy, and low cost. A variety of methods for detecting analyte-binding agent interactions have been developed. The simplest of these is a solid-phase format employing a reporter labeled analyte-binding agent whose binding to or release from a solid surface is dependent on the presence of analyte. In a typical solid-phase sandwich type assay, for example, the analyte to be measured is an analyte with two or more binding sites, allowing analyte binding both to a receptor, e.g., antibody, carried on a solid surface, and to a reporter-labeled second receptor. The presence of analyte is detected (or quantitated) by the presence (or amount) of reporter bound to solid surface. In a typical solid-phase competitive binding assay, an analyte competes with a reporter-labeled analyte analog for binding to a receptor (analyte-binding agent) carried on a solid support. The amount of reporter signal associated with the solid support is inversely proportional to the amount of sample analyte to be detected or determined. The reporter label used in both solid-phase formats is typically a visibly detectable particle or an enzyme capable of converting a substrate to an easily detectable product. Simple spectrophotometric devices allow for the quantitation of the amount of reporter label, for quantifying amount of analyte.

There is increasing interest in developing electrochemical biosensors capable of detecting and quantifying analyte-receptor binding events. A biosensor is defined as being a unique combination of a receptor for molecular recognition, for example a selective layer with immobilized antibodies, and a transducer for transmitting the interaction information to processable signals. Biosensors offer an alternative format for the performance of established immunoassays.

One general type of biosensor employs an electrode surface in combination with current or impedance measuring elements for detecting a change in current or impedance in response to the presence of a ligand-receptor binding event. This type of biosensor is disclosed, for example, in U.S. Pat. No. 5,567,301.

Biosensors based on surface plasmon resonance (SPR) effects have also been proposed, for example, in U.S. Pat. No. 5,485,277. These devices exploit the shift in SPR surface reflection angle that occurs with perturbations, e.g., binding events, at the SPR interface. Finally, a variety of biosensors that utilize changes in optical properties at a biosensor surface are known, e.g., U.S. Pat. No. 5,268,305.

The interest in biosensors is spurred by a number of potential advantages over strictly biochemical assay formats. First, electrochemical biosensors may be produced, using conventional microchip technology, in highly reproducible and miniaturized form, with the capability of placing a large number of biosensor elements on a single substrate (e.g., see U.S. Pat. Nos. 5,200,051 and 5,212,050).

Secondly, because small electrochemical signals can be readily amplified (and subjected to various types of signal processing if desired), electrochemical biosensors have the potential for measuring minute quantities of analyte, and proportionately small changes in analyte levels.

PCT patent application PCT/CA97/00275, published Nov. 6, 1997, publication No. WO 97/41424, discloses a novel electrochemical biosensor having a conductive detection surface, and a hydrocarbon-chain monolayer formed on the surface. Biosensor operation is based on the flow of an ionized redox species across the monolayer, producing a measurable current flow. In one embodiment of the biosensor disclosed, binding of an analyte to its opposite binding member attached to the surface of some of the hydrocarbon chains increases measured current flow by increasing the disorder of the monolayer, making it more permeable to the redox species. In another general embodiment, the opposite binding member is anchored to the monolayer through a coiled-coil heterodimer structure, allowing any selected binding member carried on one α-helical peptide to be readily attached to a "universal" monolayer surface carrying the opposite α-helical peptide. This biosensor is capable of detecting and quantifying analyte-binding events and is characterized by: (i) direct electrochemical conversion of the binding event to electrical signal; (ii) a high electron flow "turnover" from each binding event; (iii) adaptable to substantially any analyte, and (iv) good storage characteristics and rapid wetting with sample application.

It would be desirable to adapt this novel biosensor to a wide variety of analytes and to incorporate the biosensor into a card-based device.

SUMMARY OF THE INVENTION

In one aspect the present invention involves a pocket-sized test device which is self-contained and is capable of qualitative and/or quantitative measurement of single or multiple analytes.

In another aspect the invention provides a device which is conveniently used at the point of care or point of use, and which is sensitive, accurate, specific, and inexpensive to manufacture.

A further aspect is to provide a test card which can store the results for later retrieval and analysis.

Still another aspect is to provide a test card which can optionally be used in association with a reader device.

Yet another aspect is to provide a multi-sensor test card for detecting or quantitating a large number of different analytes from a small sample volume.

According to the invention, there is provided a diagnostic card device for use in detecting or quantitating an analyte present in a liquid sample, comprising, a card substrate having formed therein a sample introduction region, a biosensor, and a sample-flow pathway communicating between the sample-introduction region and the biosensor. Preferably, the biosensor comprises a detection surface with surface-bound molecules of a first charged, coil-forming peptide capable of interacting with a second, oppositely charged coil-forming peptide to form a stable α-helical coiled-coil heterodimer, where the binding of the second peptide to the first peptide, to form such heterodimer, is effective to measurably alter a signal generated by the biosensor, and the sample-flow pathway contains (i) a conjugate of the second coil-forming peptide and the analyte or an analyte analog, in a form releasable into the sample liquid, and (ii) an analyte-binding agent, wherein sample introduced in the sample introduction region is adapted to be carried through the sample-flow pathway, where the analyte mixes with the conjugate, and the analyte and conjugate react with the binding agent, under conditions effective to immobilize analyte and conjugate so bound. The device can include circuitry for generating an analyte-dependent electrical signal from the biosensor; and can also include a signal-responsive element for recording such signal. The device can further include a background control biosensor and a control sample-flow pathway connecting the sample-introduction region to the background control biosensor, and the control sample-flow pathway does not include the conjugate. The invention can be used in detecting or quantitating a plurality of different selected analyses, in which case the device further includes, for each analyte, (i) a separate biosensor, and (ii) a separate sample-flow pathway connecting the sample-introduction region to each associated biosensor, where each sample-flow pathway includes (a) a conjugate of the second coil-forming peptide and one of the selected analyses or analog thereof, and (b) an associated selected analyte-binding agent. The sample introduction region comprises a port communicating with each of the sample-flow pathways. The sample introduction region, sample-flow pathways and biosensors can be microfabricated on the substrate. The sample-flow pathway can include a mixing zone containing the conjugate in releasable form, and a reaction zone containing the analyte-binding agent in immobilized form.

The biosensor can further include a conductive detection surface, a monolayer composed of hydrocarbon chains anchored at their proximal ends to the detection surface, and the first charged coil-forming peptide also anchored to the surface, where the binding of the second peptide to the first peptide, to form such heterodimer, is effective to measurably alter current flow across the monolayer mediated by a redox ion species in an aqueous solution in contact with the monolayer, relative to electron flow observed in the presence of the first peptide alone. The device preferably includes circuitry which can be adapted to measure current flow across the detection surface, and output a signal related to measured current flow.

The device preferably is used in detecting the presence or amount in a sample of an analyte which forms with the analyte-binding agent, an analyte/analyte-binding agent pair. Examples of such pairs include antigen-antibody, hormone-receptor, drug-receptor, cell surface antigen-lectin, biotin-avidin, and complementary nucleic acid strands.

The signal-responsive element of the device can be a liquid crystal display device, which can be a linear color display device that responds to voltage level from the circuitry. Alternatively, the signal-responsive element can be a magnetic recording medium effective to store a measured signal value from the circuitry. The device can be used with a magnetic reader device designed to read the measured signal value stored on the medium. Alternatively, the signal-responsive element of the device is separable from portions of the card that are adapted to contact the sample, thus providing a sample-free storage record of sample diagnostic results. The sample-free storage record can comprise a magnetic recording medium effective to store a measured signal value from the circuitry.

In another aspect, the invention provides a diagnostic system for use in detecting or quantitating an analyte present in a liquid sample, comprising, (a) a device having (i) a card substrate, and formed therein a sample-introduction region, a biosensor, a sample-flow pathway communicating between the sample-introduction region and the biosensor, and (ii) conductive leads operatively connected to the biosensor, and (b) a card-reader device having (i) a card slot for introducing the card into the reader, (ii) circuitry for generating an analyte-dependent electrical signal from the biosensor, when the card is placed in the slot and the card leads are in contact with circuitry leads in the reader, and a signal-responsive element for displaying and recording such signal. The biosensor in the device preferably has a detection surface with surface-bound molecules of a first charged, coil-forming peptide capable of interacting with a second, oppositely charged coil-forming peptide to form a stable α-helical coiled-coil heterodimer, where the binding of the second peptide to the first peptide, to form such heterodimer, is effective to measurably alter a signal generated by the biosensor, and the sample-flow pathway contains (i) a conjugate of the second coil-forming peptide and the analyte or an analyte analog, in a form releasable into the sample liquid, and (ii) an analyte-binding agent, wherein sample introduced in the sample-introduction region is adapted to be carried through the sample-flow pathway, where the analyte mixes with the conjugate, and the analyte and conjugate react with the binding agent, under conditions effective to immobilize analyte and conjugate so bound. The device in this system can further include, a background control biosensor and a control sample-flow pathway connecting the sample-introduction region to the second biosensor, and the second sample flow pathway does not include the conjugate. The system can be used for detecting or quantitating a plurality of different selected analyses. In this aspect, the invention provides in the device, for each analyte, (i) a separate biosensor, and (ii) a separate sample-flow pathway connecting the sample-introduction region to each associated biosensor, where each sample-flow pathway includes (a) a conjugate of the second coil-forming peptide and one of the selected analyses or analog thereof, and (b) an associated selected analyte-binding agent.

In another aspect, the biosensor used in the diagnostic device comprises a biosensor which includes an electrode substrate with a detection surface covered by a monolayer of hydrocarbon chains. The chains are anchored at their proximal ends to the detection surface, and are sufficiently close-packed and ordered to form an effective barrier to electron flow across the monolayer mediated by a redox species in an aqueous solution in contact with the monolayer. The analyte-binding agent whose binding to an analyte is to be detected is attached to the distal ends of a portion of the monolayer chains, such that binding of an analyte to the analyte-binding agent perturbs the monolayer sufficiently to measurably increase electron flow across the monolayer mediated by such redox species.

The aqueous solution of redox species in contact with the monolayer is held in a chamber that is also designed to receive sample analyte, to bring the analyte into contact with analyte-binding agent on the monolayer. Ion-mediated electron flow across the monolayer, in response to binding events occurring between the analyte and analyte-binding agent, is measured in an electrical circuit in the apparatus. In a preferred biosensor, the monolayer is composed of 8–22 carbon atom chains attached at their proximal ends to the detection surface, e.g., a gold surface, by a thiolate linkage. The chains have a preferred molecular density of about 3 to 5 chains/nm$^2$. The dielectric constant of the monolayer in the presence of the solution of redox species, but in the absence of the analyte, is preferably less than about 2, with a change in the dielectric constant of 10% or more, by analyte binding to the analyte-binding agent, being readily detectable.

Exemplary analyte/analyte-binding agent pairs include antigen-antibody, hormone-receptor, drug-receptor, cell-surface antigen-lectin, biotin-avidin, substrate/antibody and complementary nucleic acid strands, where the analyte is typically the first-named of these pairs. Where the biosensor is used to detect a analyte or analog thereof, the biosensor may further include a analyte-binding agent which competes with the analyte or analog for binding to the analyte-binding agent on the monolayer. One exemplary analyte-binding agent is an oligosaccharide ligand, and one exemplary analyte, the Verotoxin receptor, also known "Shiga-like toxin".

The electrode employed in the biosensor used in the present invention can be prepared by (i) subjecting the conductive metal surface of the electrode substrate to mild oxidation conditions, (ii) adding to the substrate, a solution of hydrocarbon chains having lengths between 8–22 carbon atoms and derivatized at one chain end with a thiol group, and (iii) applying a positive potential to the electrode. The potential placed on the electrode is preferably at least 250 mV vs NHE (normal hydrogen electrode), in a solution containing the alkyl thiol to be deposited, and electrolytes including lithium ion and perchlorate anions. A selected portion of the hydrocarbon chains are derivatized at their ends opposite the thiol group, with the analyte-binding agent of interest. The oxidative conditions applied to the electrode surface are such as to produce deposition of a monolayer of close-packed, oriented chains on the substrate, as evidenced by the ability of the electrode to form an effective barrier to electron ion flow across the monolayer mediated by a redox ion species in an aqueous solution in contact with the monolayer.

In another preferred embodiment of the biosensor, analyte-binding agent molecules are attached to the hydrocarbon chains forming the monolayer in the electrode through a heterodimer-subunit complex composed of first and second peptides that together form α-helical coiled-coil heterodimer, where: (i) the first peptide is covalently bound to the electrode surface through a spacer, such as an oligopeptide or hydrocarbon chain; (ii) the analyte-binding agent is covalently attached to the second peptide; (iii) binding of the second peptide to the first peptide, to form such complex, is effective to measurably reduce the electron flow across the monolayer mediated by such redox ion species, relative to electron flow observed in the presence of the first peptide alone; and (iv) binding of an analyte to the analyte-binding agent, with such forming part of the complex, is effective to measurably increase the electron flow across of the monolayer mediated by such redox species.

Also contemplated is an electrode for use in a biosensor of this type, composed of a substrate having a detection surface and analyte-binding agent molecules attached to surface through an α-helical coiled-coil heterodimer of the type detailed above.

The electrode just described can be produced, in accordance with another aspect of the invention, by contacting together: (a) a detection surface having attached thereto, a first heterodimer-subunit peptide, and (b) a second heterodimer subunit capable of binding to the first subunit to form an α-helical heterodimer, and having a covalently attached analyte-binding agent capable of binding specifically to such analyte.

BRIEF DESCRIPTION OF THE DRAWING

In the drawings, which comprise a portion of this disclosure:

FIG. 27 illustrates a first method for forming a biosensor electrode having a lipid monolayer and attached ligand molecules, in accordance with the invention;

FIG. 28 illustrates a second method for forming a biosensor electrode having a lipid monolayer and attached ligand molecules, in accordance with the invention;

FIG. 29 illustrates a third method for forming a biosensor electrode having a lipid monolayer and attached ligand molecules, in accordance with the invention;

FIG. 40 is a schematic illustration of a biosensor which demonstrates ion gating effects with a negatively charged ligand in an electrode monolayer;

FIG. 41 is idealized data obtained from the biosensor of FIG. 40;

FIG. 42 is a schematic illustration of a biosensor which demonstrates ion gating effects with a positively charged ligand in an electrode monolayer;

FIG. 43 is idealized data obtained from the biosensor of FIG. 42;

FIGS. 49–53 show a synthetic pathway used for producing a trisaccharide-hydrocarbon conjugate employed in the monolayer shown in FIGS. 35–37.

DETAILED DESCRIPTION OF THE INVENTION

In one embodiment, the diagnostic card device of the present invention includes the following elements which will be further described hereinbelow: a support substrate, which includes a sample-introduction region, a biosensor, a sample-flow pathway communicating with said sample-introduction region and said biosensor; circuitry for generating an analyte-dependent electrical signal from the biosensor; and a signal-responsive element for recording such electrical signal.

Figure 3:
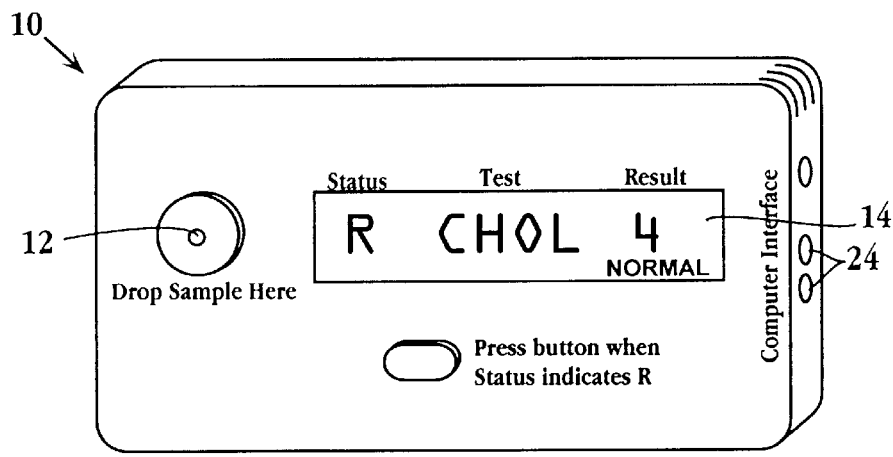
FIG. 3 is an isolated perspective view of a diagnostic device of the present invention.

FIG. 3 is a simplified external perspective view of a diagnostic device 10 in accordance with one embodiment of the present invention. The device includes a sample-introduction region 12, such as a port. The device can be of any convenient size or shape (e.g., square, round, or rectangular) which can contain the electronic components and which can be easily stored or carried by hand. For example, the general dimensions of a credit card (e.g., about 85 mm×53 mm×2 mm) would be suitable. Another example is the dimensional size of a standard PCMCIA card. The device can be used on-site in the home and in the physician's office or in a remote location.

Figure 1:
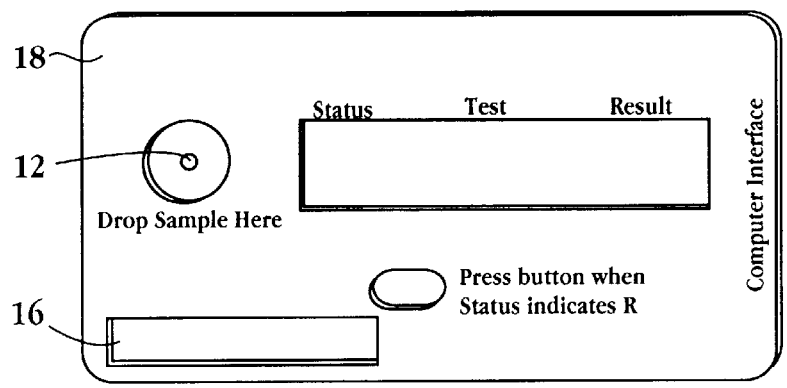
FIG. 1 is an isolated perspective view of the cover of a diagnostic device of the present invention.

The card preferably comprises a laminate structure with a cover 18 (FIG. 1) which is composed preferably of a lightweight and durable thermoplastic such as PVC, polyethylene, polypropylene, DELRIN, ABS, or polystyrene. The cover can be clear or can be color coded.

The substrate 20 is a generally planar solid support for the device, preferably composed of an electrically insulating, non-porous, rigid, moisture impermeable material. A wide variety of organic and inorganic materials, both natural and synthetic, and combinations thereof, may be employed provided only that the support does not interfere with the capillary action of the bibulous material, or non-specifically bind assay components, or interfere with the signal producing system. Illustrative polymers include polyethylene, polypropylene, poly(4-methylbutene), polystyrene, polymethacrylate, poly(ethylene terephthalate), nylon, poly (vinyl butyrate), glass, and ceramics. There are numerous methods of joining the cover 18 and support substrate 20 together which would be apparent to a person skilled in the art, including the use of a snap, an adhesive such as epoxy, hot melt glue or any commercially available glue or tape.

In the embodiment shown (FIG. 3), the device includes a visual readout display 14 such as an LCD and can indicate a variety of messages including "Status" (e.g., "R" for ready, "C" for calibrating, "S" for standby, "M" for malfunction or other messages), "Test" for indentifying the analyte being detected, and "Result" for indicating the results of the test. The results are preferably quantitatively indicated in clinically meaningful units (e.g., ug/dL) or by a number or letter associated with a graded scale. The result can be accompanied by a message such as "normal", "high" or "see your doctor". The cover can also include a label 16 for printing patient name and/or number.

The device can include activation button 22 which is depressed in order to initiate testing after application of sample. In a preferred embodiment, a pair of sensing electrodes (not shown) are provided within a sample-flow pathway in the biosensor and the presence of a liquid test sample would bridge the electrodes, reducing the resistance across the them and signaling the presence of a conductor (sample liquid) therebetween. An "R" indicating a ready status would then appear on the LCD prompting the user to begin a test by depressing button 22. Optionally, the LCD includes a linear color voltage indicator in which the alpha numeric characters appearing in the Results window are colored to correspond with the voltage (and therefore the analyte level) determined by the biosensor, e.g., red indicates high voltage, blue indicates low voltage.

Contacts 24 are provided for interfacing the test card to a reader or to a computer for downloading digital memory from the device and for further processing and display of the data.

Figure 2:
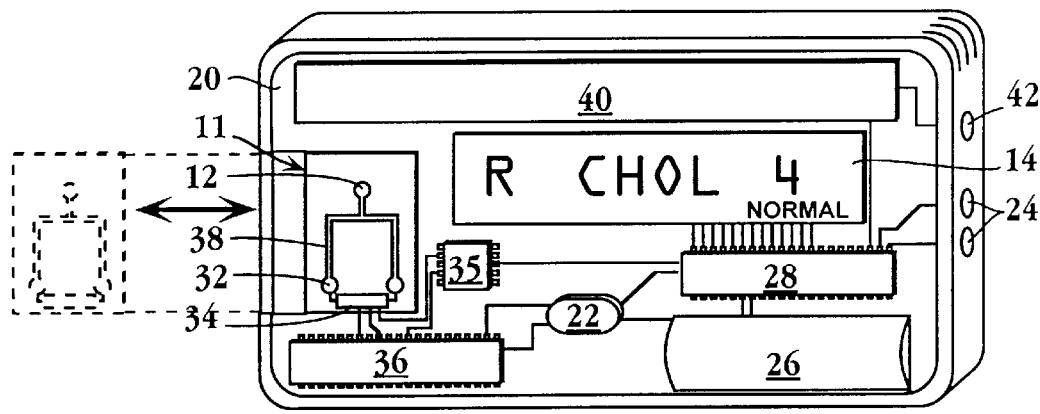
FIG. 2 is an isolated perspective view of a diagnostic device of the present invention with the cover removed.

FIG. 2 is a simplified perspective view with the cover 18 removed of the device 10 of this invention designed for measurement of a detectable signal, showing one configuration of the electronic and sample application components for analyte testing. In this embodiment, the device is self-contained and comprises integrated components.

The device preferably includes a power supply 26 such as a battery or solar cell.

The device includes a microprocessor 28 with memory which receives and processes input from the detector, stores assay calibration information and the like. The processor can be any common or custom integrated circuit with memory. It must have the capacity to either store a set of pre-programmed calibration curves or have the capability to be programmed during device manufacturing. The microprocessor can include programmable BIOS (ROM) with or without digital signal processing.

The device further includes circuitry such as an analog to digital converter 35 which receives input from the biosensor and provides output to the processor 28.

Voltage regulator 36 modulates the voltage supplied to the biosensor. The voltage can be modulated to give direct or alternating current.

During a test, analog signals from biosensor 32 are converted to digital signals by the analog-to-digital converter 35 and transmitted to microprocessor 28 which stores data indicative of the detected analyte preferably as a function of time, in RAM memory. The data can be displayed and/or stored and includes (as described hereinbelow) instantaneous current, integrated current over fixed timer period, or voltage output. This test data can be processed for comparison with standard curve data, which represents the concentration of a substance of interest. The data can be processed to determine concentration from reaction "end-point" data (i.e., data at a specified time and/or the rate of change of the reaction and/or the maximum rate of change of the reaction, as determined from measurements of the biosensor output over time). RAM memory can be provided, from interface 42 or replaceable test memory, with standard curve data for one or all of such determinations. The comparison and all necessary calculations are performed by microprocessor 28 using a program stored in memory and/or preferably replaceable test memory, and are outputted to LCD display or to a printer or other device via contacts 24. The contacts can comprise an input/output interface such as an RS-232, USB, PCMCIA or other standard link for allowing the unit to communicate with a PC both for programming the microprocessor and for logging data from the device, as described hereinbelow.

A temperature sensor (not shown) can be incorporated into the biosensor 32 to detect the temperature and provide ambient temperature information for calibration adjustment at temperature extremes.

In one embodiment, the biosensor and sample-flow pathway 38 are integrated onto substrate 20. In another embodiment, the biosensor and the sample-flow pathway are formed on a chip as described hereinbelow, which is operably attached to the substrate. The biosensor includes a sample application region such as sample-introduction region 12 aligned with the sample-application region of the cover 18.

One embodiment of the invention is an integrated assay instrument containing all electrical and chemical components required for the analysis. Results are displayed in the LCD. The data can be transferred to magnetic or other recording media via contacts 42.

The processor will also control the entire operation of the instrument including indicating a ready status, recording, determining when the reaction has stabilized, receiving and processing information from the temperature sensor; receiving input from the biosensor and converting it to output, based on calibration information, to the display.

Figure 4:
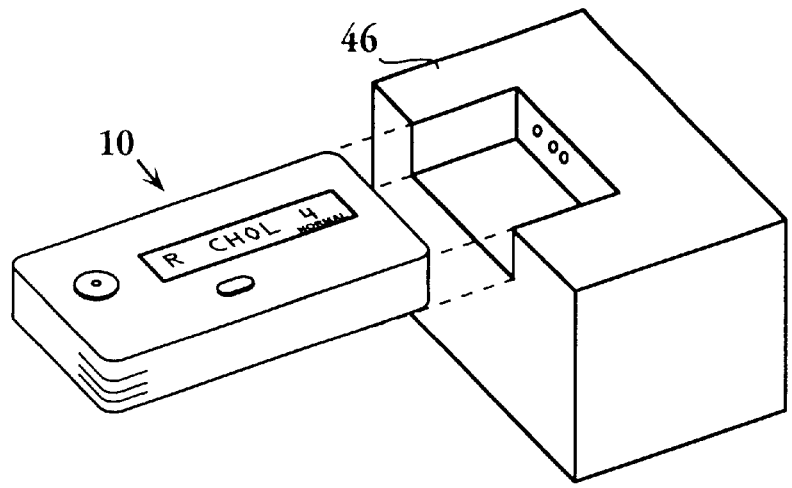
FIG. 4 is a perspective view of a diagnostic device of the present invention used in conjunction with a reader.

In another embodiment of the invention (FIG. 4) the test card is designed to be used in conjunction with a reader 46. In this embodiment, the card 10 includes a signal responsive element for recording a signal from the biosensor. For example, the signal responsive element can comprise a magnetic recording medium 40 effective to store a measured signal value from the circuitry (e.g., from the analog to digital converter) of the device. Examples of recording media include any suitable medium, including but not limited to magnetic recording medium, EPROM, battery-backed RAM, FRAM, or "FLASH" memory for later downloading and analysis designed to be used in conjunction with a magnetic reader device 46 to read the measured signal value stored on the magnetic medium 40.

Figure 5:
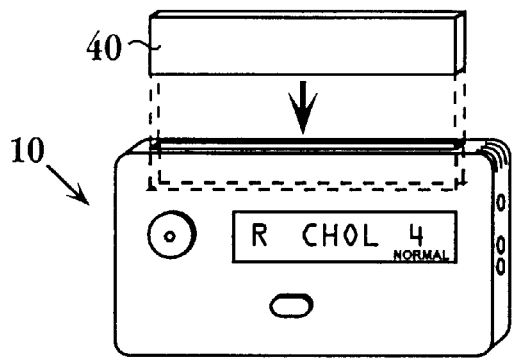
FIG. 5 is a perspective view of an embodiment of a sample responsive element which is separable from portions of the card.

In another embodiment, the sample responsive element is separable from the portions of the card that are adapted to contact the sample, to provide a sample-free storage record of the sample diagnostic results. An example of a sample responsive element is a magnetic recording medium 40 (e.g., Flash memory, EPROM, magnetic recording medium) which is separable from portions of the card as shown in FIG. 5. As another example, the portions of the card that are adapted to contact the sample are contained within a detachable biosensor module (FIGS. 2, 8A).

Figure 7:
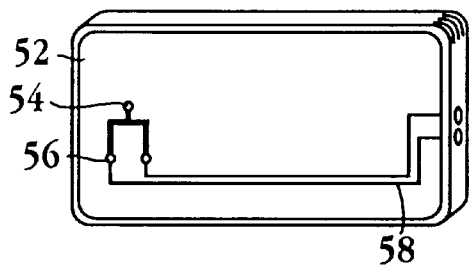
FIG. 7 is a perspective view of a diagnostic device of FIG. 6 but with the cover removed.
Figure 6:
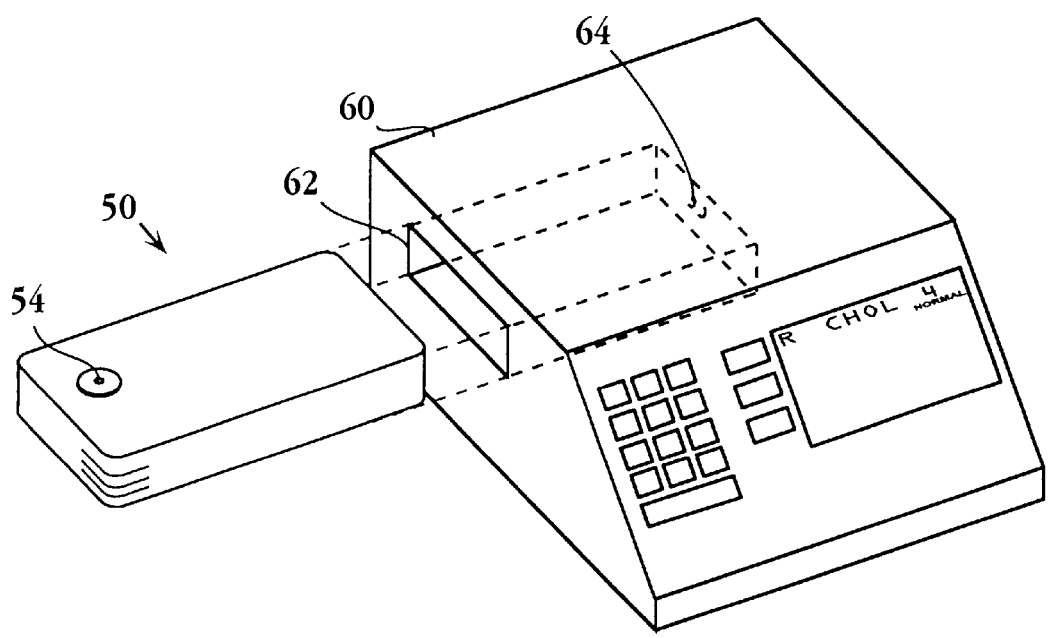
FIG. 6 is a perspective view of a diagnostic device of the present invention used with a card reader.

In yet another embodiment (FIGS. 6 and 7), the card 50 comprises a card substrate 52 which has formed therein a sample-introduction region 54, a biosensor 56, a sample-flow pathway 58 communicating between the sample-introduction region and the biosensor, and conductive leads 58 operatively connected to the biosensor. Thus, the card 50 lacks components such as processor, power supply voltage regulator, analog to digital converter, memory, and display which instead are incorporated into a card reader device 60 which provides these additional electrical components (FIG. 6). The card-reader device has a slot 62 for introducing the card into the reader and circuitry (not shown) for generating an analyte-dependent electrical signal from the biosensor when the card is placed in the slot and when the card leads are in contact with circuitry leads 64 in the reader. As an example, the diagnostic card can have the dimensions of a standard PCMCIA card, and the card slot 62 can be the PCMCIA slot of a microcomputer. An advantage of this non-integrated embodiment includes simplicity of design and savings in cost of manufacture of the card.

The device can include, in conjunction with the sample-introduction region, means for sample pre-treatment, such as filters for red blood cells (U.S. Pat. Nos. 5,658,444; 5,837,546; 5,747,274). The device can include a separation device for filtering the sample from unwanted contaminants such as red cells in blood can be constructed using synthetic membranes, fibrous depth filters such as glass fiber, plastic fiber, metal fiber, celluose fiber or any combination of filters and membranes. The separation material may be untreated or can be coated with protein, dextran, sugars, or carbohydrates for red cell stabilization, LDL, precipitation reagents such as magnesium chloride and dextran sulfate, antibodies or red cell agglutinination agents to facilitate red cell removal. Sample pretreatment can also adjust the pH to within a specific range, reference salt concentration, turbidity and or viscosity, and/or reduce or remove interfering substances such as immunochemical cross-reactants, redox substances and the like.

Figure 8A:
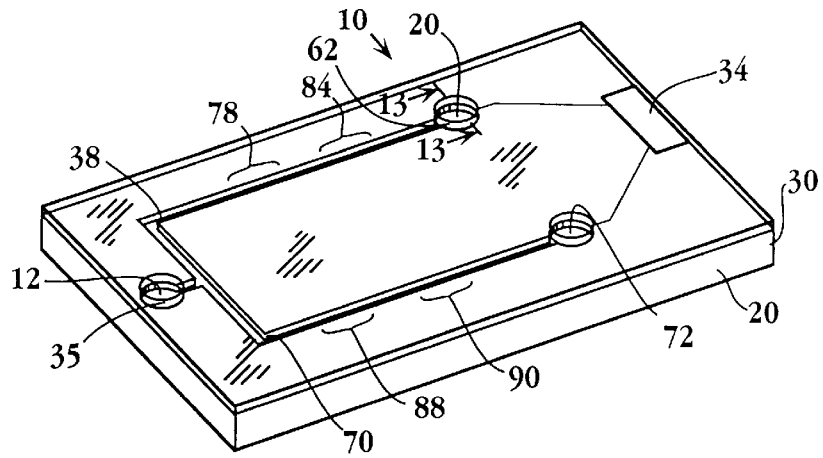
FIG. 8A is a simplified, partly schematic perspective view of a first embodiment of a biosensor module of the device of FIG. 2 showing the sample-flow pathway and biosensor.
Figure 9:
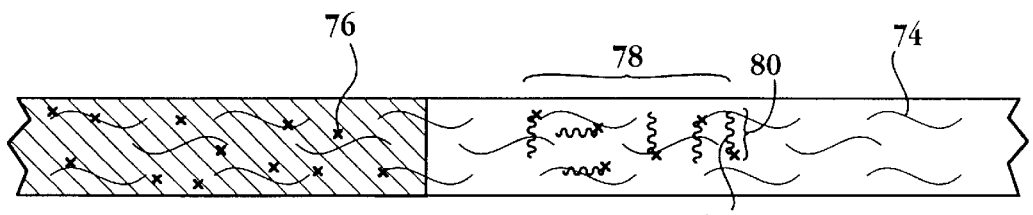
FIG. 9 is a partly schematic view of a mixing zone in a diagnostic device of FIG. 8A.
Figure 10:
FIG. 10 is a partly schematic view of a mixing zone in a diagnostic device of FIG. 8A indicating the migration of test sample as a cross-hatched area.
Figure 11:
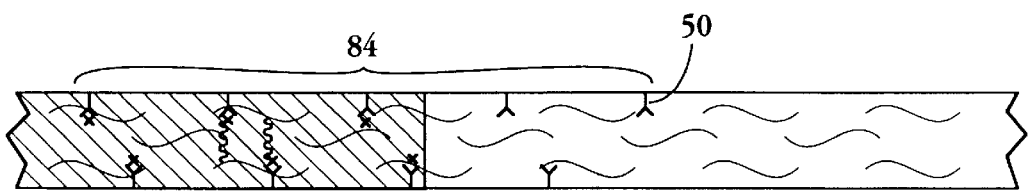
FIG. 11 is a partly schematic view of a reaction zone in a diagnostic device of FIG. 8A.
Figure 12:
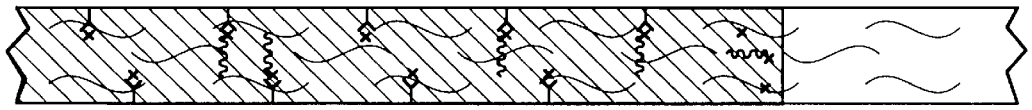
FIG. 12 is a partly schematic view of a reaction zone in a diagnostic device of FIG. 8A indicating the migration of test sample as a cross-hatched area.

Turning attention now to the sample-flow pathway and biosensor of the present invention, FIG. 8A represents a simplified and enlarged perspective view of an embodiment of the biosensor and sample-introduction elements as indicated by the section of the device 10 outlined by a dashed line in FIG. 2. The embodiment includes substrate 20, sample-introduction region 12, sample-flow pathway 38, and a biosensor 32. Details of each element are further described hereinbelow. The device preferably includes a control sample-flow pathway 70 and background control biosensor 72.

Before proceeding further with the description of the specific embodiments of the present invention, a number of terms will be defined.

"Analyte" is defined as the compound or composition to be measured, which is a member of a specific binding pair (sbp) and may be a ligand, which is mono- or poly-valent, usually antigenic or haptenic, a single or plurality of compounds which share at least one common epitopic or determinant site, or a receptor.

"Analyte-binding agent" is defined as any compound or composition capable of recognizing a particular spatial and polar organization of an analyte molecule, e.g., epitopic or determinant site. The device of the present invention can be used in detecting the presence or amount in a sample of an analyte which forms with an analyte-binding agent, an analyte/analyte-binding agent pair. Non-limiting examples of such pairs include antigen-antibody, hormone-receptor, drug-receptor, cell surface carbohydrate-lectin, biotin-avidin, and complementary nucleic acids. Numerous examples of such pairs are known (e.g., as described in U.S. Pat. No. 5,716,778 (1998) to Ullman).

"Analyte analog" is defined as a modified analyte which can compete with the analogous analyte for a receptor, the modification providing means to join an analyte analog to another molecule.

"Bibulous material" is defined as a porous material having pores of at least 0.1 $\mu$m, preferably at least 1.0 $\mu$m, which is susceptible to traversal by an aqueous medium in response to capillary force. Such materials are generally hydrophilic or are capable of being rendered hydrophilic and include inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross-linked dextran, agarose, polyacrylate, etc.; either used by themselves or in conjunction with other materials; ceramic materials; and the like. The bibulous material can be attached to a support. The bibulous material may be polyfunctional or be capable of being polyfunctionalized to permit covalent bonding of compounds as described hereinbelow.

Binding of molecules to the bibulous material may be accomplished by well-known techniques, commonly available in the literature. See, for example, "Immobilized Enzymes," Ichiro Chibata, Halsted Press, New York (1978) and Cuatrecasas, et al., J. Bio. Chem., 245:3059 (1970).

The bibulous material can be a single structure such as a sheet cut into strips or it can be particulate material bound to a support or solid surface. In one embodiment, the material is applied using a screen printing technique, such as described in U.S. Pat. No. 5,736,188.

The substrate 20 is a generally planar solid support for the device, preferably composed of an electrically insulating, non-porous, rigid, moisture impermeable material. A wide variety of organic and inorganic materials, both natural and synthetic, and combinations thereof, may be employed provided only that the support does not interfere with the capillary action of the bibulous material, or non-specifically bind assay components, or interfere with the signal producing system.

Sample-introduction region 12 provides a site for application of a liquid sample containing analyte 76 (FIGS. 9–12). As used herein, "liquid sample" typically refers to a naturally occurring or artificially formed liquid test medium suspected of containing the analyte of interest. The liquid sample may be derived from a wide variety of sources such as physiologic fluid illustrated by blood, serum, plasma, urine, occular lens fluid, saliva, amniotic and spinal fluid, etc., food products such as milk or wine, chemical processing streams, or waste water, etc. The volume of sample can vary between 10–200 μL. In a preferred embodiment, the sample-introduction region is an inlet port which is in liquid communication with the with sample-flow pathway 38.

The sample-flow pathway 38 is preferably a channel or conduit between the sample-introduction region 12 and the biosensor 32. In one embodiment, the sample-flow pathway is an essentially unblocked passage or trench of a diameter suitable for conveying the liquid sample by capillary migration from the sample application region to the biosensor 32. Such a microfluidic trench can be formed by micromachining substrate material, e.g., as described in U.S. Pat. No. 5,194,133 or by injection molding. Liquid sample migrates in the sample flow pathway by capillary action or is driven by a micro-pump or by electroosmotic flow induced by suitably placed electrodes. As described hereinbelow, assay reagents are bound either in a releasable form or immobilized within the pathway 38. For example, the reagents can be bound to the walls of the pathway 38. In a preferred embodiment, along the length of the sample-flow pathway 38 is an insoluble bibulous material 74 for conveying the sample by capillarity and for binding assay reagents either in a releasable form or an immobilized form.

Downstream of the sample-introduction region 12, the sample-flow pathway includes a mixing zone (or mixing chamber) 78. The mixing zone contains a conjugate 80 consisting of the analyte (or analyte analog) 76 linked to a charged coil-forming peptide 82. Peptide 82 is selected for forming a heterodimer with an oppositely charged coil-forming peptide which is anchored within the biosensor 32, as described hereinbelow. Conjugate 80 is provided in mixing zone 78 in a form which is releasable, i.e., diffusible, into the sample liquid when sample is drawn, e.g., by capillarity, into the mixing zone. For example, conventional methods are used for releasably binding the conjugate to the bibulous material, such as the spot and dry method as described in U.S. Pat. No. 5,580,794 (which is incorporated by reference in its entirety herein) or using an applicator such as the Bio Dot dispenser (Bio Dot, Inc. Irvine, Calif.).

Downstream of the mixing zone 78 is reaction zone (or reaction chamber) 84 (FIGS. 8, 11 and 12) in which analyte-binding agent 86 is immobilized within the pathway 38. In one embodiment, the analyte-binding agent is an antibody to the analyte. The immobilization of proteins onto glass and other surfaces, are known (e.g., as discussed in U.S. Pat. No. 5,192,507, which is incorporated by reference in its entirety herein). Immobilization of molecules to a bibulous material is performed using conventional methods such as a soak and dry immobilization method.

During the passage of liquid sample through the binding zone 84, analyte 76 and conjugate 80 react with the binding agent 86 under conditions effective to immobilize analyte or conjugate so bound to the binding agent. In a preferred embodiment of the invention, the device further includes a control sample-flow pathway 70 having a control mixing zone 88 and control binding zone 90, in liquid communication with the sample-introduction region 12 and a background control biosensor 72. Preferably, the control sample-flow pathway lacks the conjugate in the control mixing zone 88, but is otherwise similar to the sample-flow pathway 38.

It will be appreciated from the discussion hereinabove that due to competitive binding in binding zone 84, there will be an inverse relationship between the amount of analyte in a liquid sample and the amount of conjugate 80 bound in zone 88. Sample liquid flowing downstream from zone 84 contains conjugate 80 not bound in zone 84. Thus, there is a positive relationship between the level of conjugate in the liquid emerging downstream from zone 84 and the level of analyte in the original liquid sample. The amount of reagents, such as binding agent 86 and conjugate 80, provided within the sample-flow pathway is predetermined by optimization methods well known in the art. For example, in the absence of analyte, the amount of binding agent 86 in zone 84 preferably is just sufficient to bind all of conjugate 80.

In general, the biosensor of one embodiment of the invention has a detection surface with surface-bound molecules of a first charged, coil-forming peptide capable of interacting with a second, oppositely charged coil-forming peptide to form a stable alpha-helical coiled-coil heterodimer. The two oppositely charged peptides spontaneously self-assemble into a heterodimer complex. In one embodiment, the invention employs an electrochemical biosensor which measures current flow across a hydrocarbon-chain monolayer, anchored to the detector surface, mediated by redox species in aqueous solution in contact with monolayer relative to electric flow observed in the absence of analyte-peptide conjugate. Other embodiments employ a surface plasmon resonance biosensor, as described hereinbelow.

In a general embodiment of the invention, a first charged coil-forming peptide 98 (FIGS. 13–15) is anchored to the biosensor surface. A second charged coil forming peptide 82 is linked to analyte (or analog) as a conjugate 80. The peptides 98 and 82 form a heterodimer and are two non-identical, preferably oppositely charged polypeptide chains, typically each about 21 to about 70 residues in length, having an amino acid sequence compatible with their formation into stable two-stranded α-helical heterodimeric coiled-coils. They are designated herein as HSP1 (heterodimer-subunit peptide 1), and HSP2 (heterodimer-subunit peptide 2). In the discussion below, HSP1 will refer to the peptide attached to the biosensor surface in the biosensor, and HSP2, to the peptide having an attached analyte. It will be understood that these designations refer to the functional role played by the subunit peptide, not the actual peptide sequence.

Figure 8B:
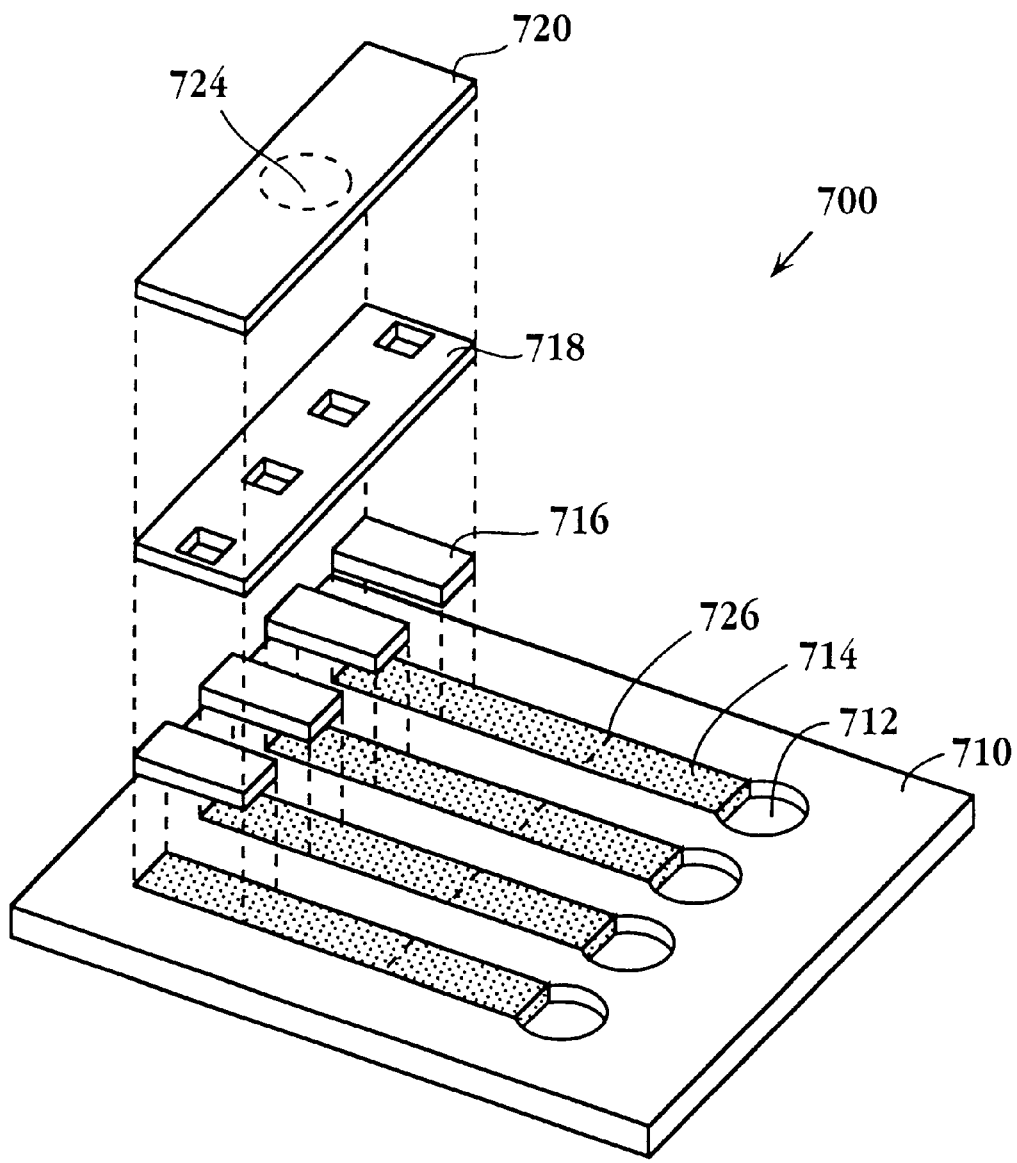
FIG. 8B is an exploded view of a second embodiment of a biosensor module.
Figure 22:
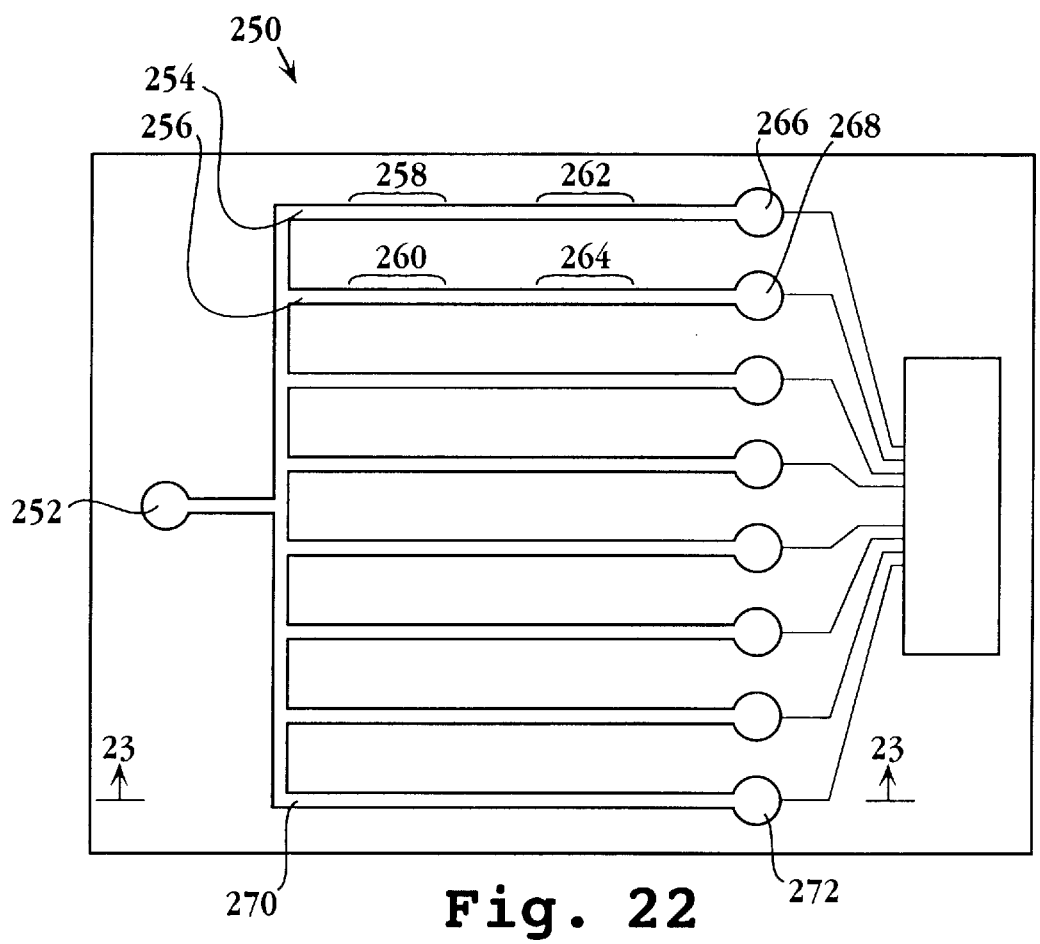
FIG. 22 is a simplified, partly schematic view of the top side of a multi-analyte detection device in accordance with one aspect of the invention.

Another embodiment of a biosensor module for use with the present invention is shown in FIG. 8B. In analogy with module 11, module 700 includes a substrate 710, biosensor 712, sample flow path 714 comprising a bibulous material, a conjugate pad 716, a plastic (e.g., polyurethane) spacer 718, filter element 720. The conjugate pad contains diffusively bound conjugate. The flow path 714 comprises a bibulous matrix containing non-diffusively bound analyte binding agent. Sample introduced at a sample application area 724 (aligned with port 12 in FIG. 3) permeates the filter 720 which serves to remove particulate matter, such as cells. Spacer 718 facilitates the distribution of the fluid flowing from filter 720 into pad 716. The fluid mixes with HSP2/analyte conjugate in pad 716 and enters matrix 714 which includes a mixing zone 726. The fluid emerging from the matrix 714 enters biosensor 712 as described hereinabove. The module preferably includes a background control biosensor and a positive control biosensor in analogy with devices 11 (FIG. 8A) and 250 (FIG. 22) as described herein.

Figure 8C:
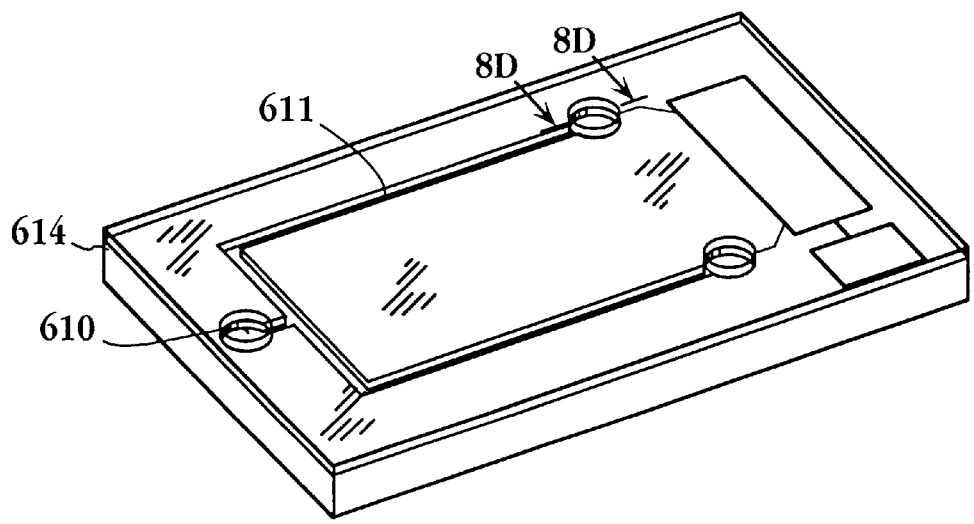
FIG. 8C is a simplified, partly schematic perspective view of a third embodiment of a biosensor module of the device of FIG. 2.
Figure 8D:
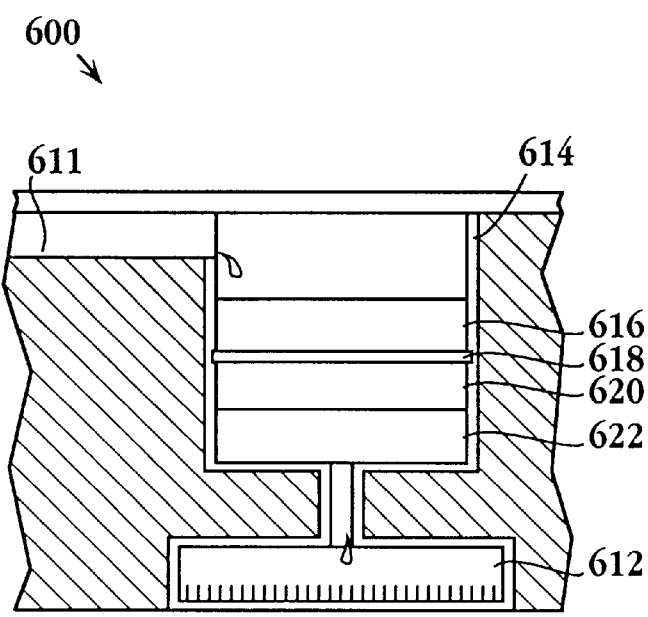
FIG. 8D is a schematic and enlarged diagram of a side view of a section of the module of FIG. 8C taken along the arrows 8D.

Yet another embodiment of a biosensor module is shown in FIGS. 8C,8D. The device 600 includes a sample application port 610, microchannel 611, housing 614, biosensor chamber 612, filter element 616, porous support element 618, conjugate pad 620, and matrix element 622. Sample introduced at a sample application port 610 enters the top of the device and permeates the filter 616 which serves to remove particulate matter, such as cells. The conjugate pad 620 contains diffusively bound conjugate. Matrix 622 comprises a bibulous matrix containing non-diffusively bound analyte binding agent. Support element 618 supports the filter 616 and has openings therethrough for downward transfer, under the influence of gravity and also capillary action, of fluid from filter 616 into conjugate pad 620. The fluid mixes with HSP2/analyte conjugate in pad 620 and enters matrix 622. The fluid emerging from the matrix 622 enters biosensor 612. A plurality of separate biosensors can be arranged, preferably on a planar substrate, to receive sample fluid delivered from microchannels emanating from a central sample application area (FIG. 8C). The module preferably includes a background control biosensor and a positive control biosensor in analogy with devices 11 (FIG. 8A) and 250 (FIG. 22) as described herein.

Figure 13:
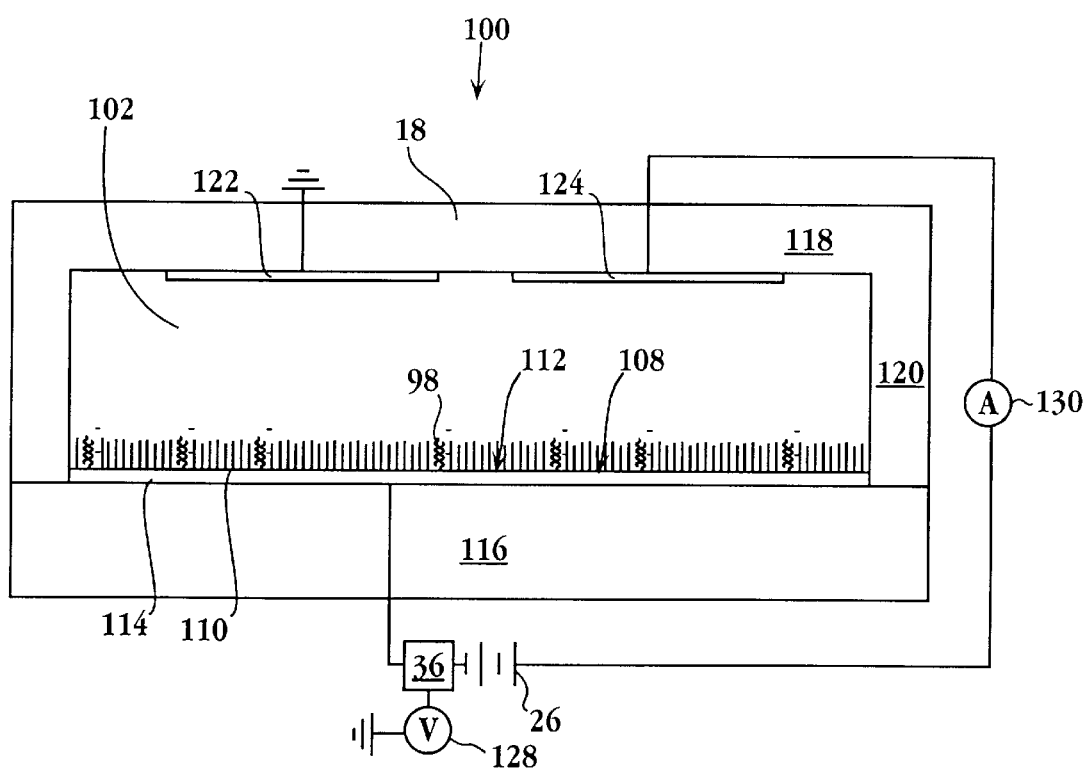
FIG. 13 is a cross-sectional view taken in the direction of arrows 13—13 in FIG. 8A of a biosensor constructed in accordance with one embodiment of the invention.

FIG. 13 shows a simplified schematic view of an electrochemical biosensor 100 for detecting an analyte-peptide conjugate in a liquid medium, in accordance with the invention. The biosensor includes a chamber 102 that is in liquid communication with the sample-flow pathway of the device via opening 104. Although not shown, the chamber can include a second port or vent to facilitate liquid flow through the port. The biosensor 100 includes a working electrode 108 having a conductive detection surface 110, and, in a preferred embodiment, a hydrocarbon-chain monolayer 112 formed on the detection surface. In the embodiment shown, the detection surface is the upper surface of a conductive film 114 deposited on substrate 116. Details of the monolayer formed on the detection surface, and the method of forming the monolayer on the surface, are discussed below. In one embodiment, the substrate 116 is contiguous with substrate 20. In another embodiment, the biosensor, sample-flow pathways and sample-introduction region (FIG. 2) are assembled on a detachable module 11 which can be operatively mounted to substrate 20 of the device.

A cover 18 in the device has an upper wall 118, and side walls, such as wall 120, which are joined to edge regions of the substrate to form a closed chamber 102 therewith. The chamber serves to hold an aqueous solution required for biosensor operation, as will be described.

A reference electrode 122 and a counter electrode 124 in the apparatus are provided on the chamber-facing surface of wall 118, as shown, and are thus both in conductive contact with electrode 108 when the chamber is filled with an electrolyte solution. In the device of the invention, the sample liquid enters the chamber through an opening such as shown at 104 downstream from the mixing zone. In a preferred embodiment, electrolyte reagents are provided within the chamber preferably in a dry form that is readily dissolved within the sample fluid. For example, reagents can be lyophilized and deposited, or spotted and dried, in the reaction chamber or in the sample-flow pathway as described in U.S. Pat. No. 5,580,794. The liquid entering the chamber mixes with ionic species capable of undergoing a redox reaction, i.e., losing or gaining an electron, at a suitably charge electrode. Exemplary redox species are $Fe(CN)_6^{3-/4-}$, as a negatively charged species, and $Ru(NH_3)_6^{2+/3+}$ as a positively charged species. Other probes which can be used include $Mo(CN)_6^{3-}$ ($E_0$=+800 mV), $W(CN)_6^{3-}$ ($E_0$=+580 mV), $Fe(CN)^{4-}$ ($E_0$=+580 mV), $Ce^{4+/3+}$, ($E_0$=+1.4V), and $Fe^{+3/2+}$ ($E_0$=+666 mV). Typical redox ion concentrations are between 0.01 and 10 mM. The solution is contained in chamber 102 and is in contact with reference and counter electrodes.

The voltage potential placed on the electrode, i.e., between the electrode and reference electrode, is typically at least 90 mV above the electrochemical potential ($E_0$) value of the redox species, for oxidation, and at least 90 mV below the electrochemical potential, for reduction of the species. Consider, for example, $Fe(CN)_6^{3-/4-}$, with an $E_0$ of 450 mV (vs. NHE). Above about 550 mV electrode potential, any $Fe^{2+}$ species is oxidized to $Fe^{3+}$, and at an electrode potential below about 350 mV, $Fe^{+3}$ is reduced to $Fe^{+2}$. Similarly, $Ru(NH_3)_6^{2+/3+}$ has an $E_0$ of +50 mV (vs. NHE), so oxidation is achieved at an electrode potential above about +150 mV, and reduction, below about −50 mV.

The reference electrode 122, which is held at ground, serves as the voltage potential reference of the working electrode 108 when a selected potential is placed on the working electrode by a voltage source 126. This potential is measured by a voltage measuring device 128 which is preferably connected via connector 34 to a voltage modulator 36 (FIGS. 2, 13) which can be used to maintain the potential at a selected voltage, typically between about −500 to +800 mV.

Voltage source 26 is connected to counter electrode 124 through a current measuring device 130 as shown, for measuring current flow between the two electrodes during biosensor operation. The reference and counter electrodes are Pt, Ag, Ag/AgCl, or other suitable electrodes. the reference and working electrodes, the circuitry connecting them to the working electrode, and voltage source, are referred to herein, collectively, as circuitry for generating an analyte-dependent electrical signal from the biosensor. The signal is due to a change in current flow in response to heteroduplex formation between HSP2-analyte conjugate 80 and a charged, coil-forming peptide HSP1 98 anchored to the surface 110 of the working electrode 108. In the diagnostic card of the present device, the current measuring device 130 preferably includes an A/D converter 35 connected as described hereinabove.

Figure 14:
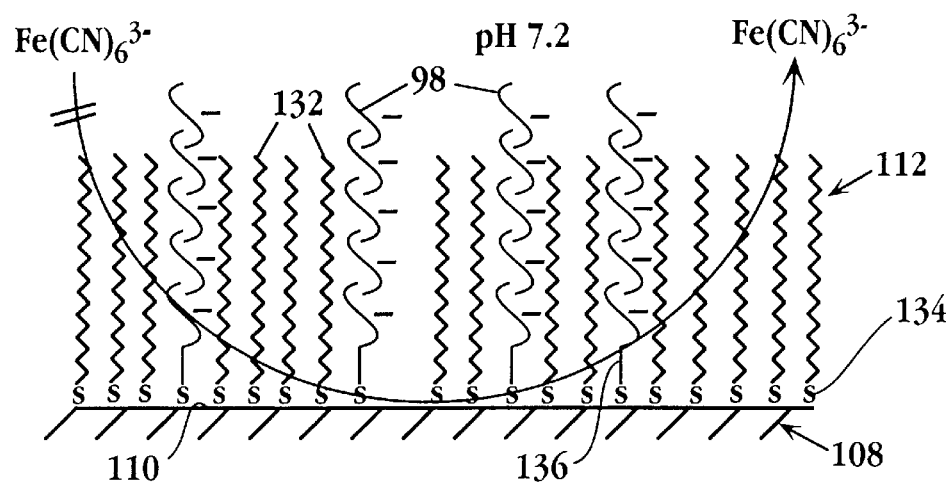
FIG. 14 is an enlarged view of a region of the electrode in the biosensor shown in FIG. 13.
Figure 15:
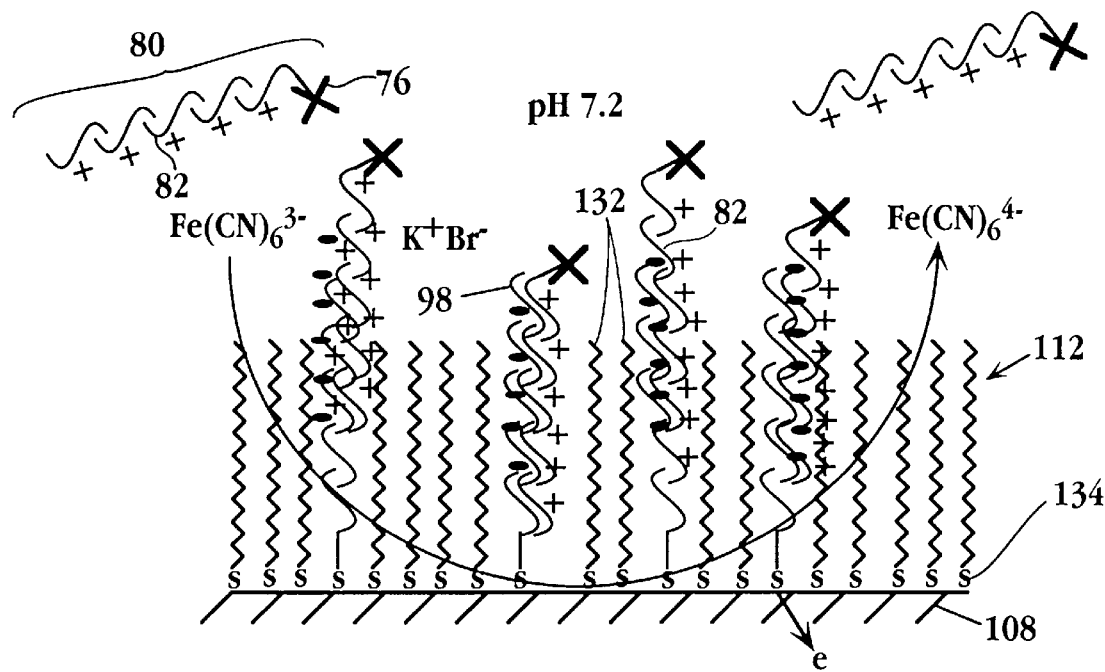
FIG. 15 is an enlarged view of a region of the electrode in the biosensor shown in FIG. 13 in the presence of HSP2-analyte conjugate.

FIGS. 14,15 are an enlarged view of a portion of the working electrode 108 having a conductive detection surface 110 and a hydrocarbon-chain monolayer 112 formed on the detection surface. The chains forming the monolayer are typically 8–22 carbon, saturated hydrocarbon chains, although longer chains, chains with some unsaturation, chains with non-carbon chain atoms, such as lipid ethers, and/or chains with minor branching, such as by non-chain methyl groups, may be employed, within the constraint that the chains, at a sufficient packing density, form a sufficiently close packed and ordered monolayer to be effective as a barrier to electron flow, under biosensor operating conditions, as discussed below. This density is calculated to be between 3–5 chains/$nm^2$.

In the embodiment shown in FIGS. 14,15, the chains 132 are coupled to the electrode detecting surface through sulfhydryl linkages 134, although other suitable coupling groups may be employed. One method for producing monolayers having suitable hydrocarbon chain densities is passive diffusion of chains onto the surface of an electrode. A preferred method consists of actively driving the chains onto the surface by applying a positive voltage potential to the conductor surface. The latter method achieves rapid monolayer formation and highly reproducible electrode characteristics.

In a preferred embodiment of the invention, the hydrocarbon-chain mixture which is actively driven onto the conductor surface includes peptide HSP1 peptide 98 that is capable of forming a stabilized, alpha-helical peptide heterodimer with an oppositely charged, complementary subunit, HSP2 such as at 82. Such heterodimer subunits are described in PCT patent application WO 95/31480 "Heterodimer Polypeptide Immunogen Carrier Composition and Method", publication date Nov. 23 1995, which is incorporated herein by reference. Exemplary subunits are referred to herein as K-coils, referring to positively charged subunits whose charge is provided dominantly by lysine residues, and E-coils, referring to negatively subunits whose charge is provided dominantly by glutamic acid residues.

HSP1 peptide 98 can be attached to the distal end of a short hydrocarbon chain (end opposite the chain's thiol group) by suitable lipid-to-peptide conjugation, e.g., by ester linkage to a hydrocarbon fatty acid. Alternatively, the peptide may be linked to the electrode surface through a peptide spacer, e.g., a tripeptide spacer that extends from one end of the subunit and includes cysteine as a terminal residue, for sulfhydryl attachment to the electrode surface. In both cases, the modified peptide is mixed with the hydrocarbon chains, at a selected mole ratio, then driven into a monolayer formation by applying a positive voltage to the electrode, resulting in a densely packed hydrocarbon-chain monolayer 112 which includes charged, coil-forming peptide 98 embedded in the planar chain matrix, while still retaining a low dielectric barrier to ion flow through the monolayer. The HSP1 peptide 98 is included in the monolayer in a mole ratio peptide/hydrocarbon chains of preferably between 1:100 to 1:5.

In a preferred method for forming the monolayer, a mixture of thiol-containing chains and thiol-terminated HSPI peptide, at a selected mole ratio, is actively driven to the surface by applying a positive voltage potential to the substrate surface, e.g., gold film. In practice, the hydrocarbon chain mixture (about 1 mM hydrocarbon chains) in an ethanolic solution of 100 mM Li perchlorate, neutral pH, is placed over the electrode, and a selected potential is applied to the electrode. The buildup of the monolayer can be monitored by increase in layer thickness. Alternatively, monolayer formation is monitored by measuring current across the monolayer, as described below. In this case, formation of the monolayer will be characterized by a steady drop in electrode current, until minimum current is reached, at which point maximum chain packing has been achieved.

Active deposition of the C16 and peptide subunit can be carried out sequentially in addition to the "mixed mode", or simultaneous deposition, described hereinabove. The conditions for the sequential deposition are essentially the same except that the peptide subunit is deposited first and the C16 subsequently.

The time required to achieve saturation packing density will vary with applied voltage, and can be as short as 10 seconds—about 4 orders of magnitude faster than monolayer formation by diffusion. Complete or nearly complete monolayer formation (30 Å thickness) occurs within 10 minutes at about 1V potential and above. At lower positive voltages, additional reaction time is required. Preferably the voltage applied to the electrode is at least between about +250 mV relative to a normal hydrogen electrode (+250 vs. NHE) and 1.2V (vs. NHE).

Not only are rapid monolayer formation times achieved, but the percentages of peptide and hydrocarbon chains present in the reaction mixture are precisely represented in the monolayers, giving highly reproducible electrode characteristics.

Methods for forming a monolayer are further described hereinbelow with reference to other embodiments of the biosensor.

In aqueous medium, the isolated heterodimer-subunit peptides are typically random coils. When HSP1 and HSP2 are mixed together under conditions favoring the formation of α-helical coiled-coil heterodimers, they interact to form a two-subunit α-helical coiled-coil heterodimeric complex. Peptides in an α-helical coiled-coil conformation interact with one another in a characteristic manner that is determined by the primary sequence of each peptide. The tertiary structure of an α-helix is such that 7 amino acid residues in the primary sequence correspond to approximately 2 turns of the α-helix. Accordingly, a primary amino acid sequence giving rise to an α-helical conformation may be broken down into units of 7 residues each, termed heptads. The heterodimer-subunit peptides are composed of a series of heptads in tandem. When the sequence of a heptad is repeated in a particular heterodimer-subunit peptide, the heptad may be referred to as a "heptad repeat", or simply "repeat".

The dimerization of HSP1 and HSP2 is due to the presence of a repeated heptad motif of conserved amino acid residues in each peptide's primary amino acid sequence. Repeating heptad motifs having appropriate amino acid sequences direct the HSP1 and HSP2 polypeptides to assemble into a heterodimeric α-helical coiled-coil structure under permissible conditions. The individual α-helical peptides contact one another along their respective hydrophobic faces.

HSP1 and HSP2 may assemble into a heterodimer coiled-coil helix (coiled-coil heterodimer) in either parallel or antiparallel configurations. In a parallel configuration, the two heterodimer-subunit peptide helixes are aligned such that they have the same orientation (amino-terminal to carboxyl-terminal). In an antiparallel configuration, the helixes are arranged such that the amino-terminal end of one helix is aligned with the carboxyl-terminal end of the other helix, and vice versa.

Heterodimer-subunit peptides designed in accord with the guidance presented in the above-referenced PCT application typically show a preference for assembling in a parallel orientation vs. an antiparallel orientation. For example, the exemplary peptides identified by SEQ ID NO:1 and SEQ ID NO:2 form parallel-configuration heterodimers as do other peptide sequences (as discussed in the PCT application). When attaching an analyte to HSP2, it is generally desirable to attach the analyte at or near the end of the peptide that will form the distal end of the heterodimer. In particular, where the heterodimer forms a parallel configuration, the HSP1 peptide is preferably anchored to the biosensor surface at its C terminus, and the analyte conjugated to the HSP2 peptide at its N terminus.

As just noted, one of the two subunit peptides (HSP1) in the heterodimer is anchored to the biosensor surface, and the second peptide (HSP2) contains an analyte intended to participate in a binding reaction in the binding zone of the device. In both cases, the peptide is synthesized, or derivatized after synthesis, to provide the requisite attachment function and analyte, respectively.

Considering the modification of HSP1, the peptide may be synthesized, at either its N or C terminus, to carry additional terminal peptides that can function as a spacer between the biosensor surface and the helical-forming part of the peptide. Alternatively, the HSP1 peptide can be attached to the biosensor surface thorough a high-affinity binding reaction, such as between a biotin moiety carried on the peptide and an avidin molecule covalently attached to the surface.

Where HSP1 is embedded in a hydrocarbon-chain monolayer (FIGS. 14,15) the spacer anchoring the HSP1 peptide to the biosensor surface may be a hydrocarbon chain. The chain is preferably a fractional length of the chains making up the bilayer, such that the distal ends of the heterodimer which forms upon binding of the two peptides in the assembled monolayer are at or near the exposed surface of the monolayer. Thus, for example, if the monolayer is made up of 18-carbon chains, the spacer is preferably 2–10 carbons in length, depending on the length of the heterodimer.

The hydrocarbon-chain spacer, in the form of a omega-thio fatty acid, may be coupled to a terminal hydroxyl or amine coupling during solid-phase synthesis, as outlined above. The derivatized peptide, in turn, can be attached to a metal surface by standard thiolate coupling (Dakkouri, et al., *Langmuir* (1996) 12:2849–2852).

Where the analyte is a polypeptide, the analyte can be synthesized by either solid-state or recombinant methods, to include the peptide analyte at the end of the HSP2 peptide that will orient distally in the assembled heterodimer. Where the analyte is a non-peptide moiety, e.g., a non-peptide hormone, drug, or nucleic acid, the HSP2 peptide can be synthesized to include one or more residues that can be specifically derivatized with the analyte. In forming the conjugate, such as 80, the analyte is preferably covalently attached to the N-terminal amino acid residue, or to one of the residues facing the exposed face of the heterodimer. Preferred coupling groups are the thiol groups of cysteine residues, which are easily modified by standard methods. Other useful coupling groups include the thioester of methionine, the imidazolyl group of histidine, the guanidinyl group of arginine, the phenolic group of tyrosine and the indolyl group of tryptophan. These coupling groups can be derivatized using reaction conditions known to those skilled in the art.

To bind the analyte-HSP2 conjugate 80 to the surface-immobilized HSP1 peptide 98, the two peptides are contacted under conditions that favor heterodimer formation. A medium favoring coiled-coil heterodimer formation is a physiologically-compatible aqueous solution typically having a pH of between about 6 and about 8 and a salt concentration of between about 50 mM and about 500 mM. Preferably, the salt concentration is between about 100 mM and about 200 mM. An exemplary benign medium has the following composition: 50 mM potassium phosphate, 100 mM KCl, pH 7. Equally effective media may be made by substituting, for example, sodium phosphate for potassium phosphate and/or NaCl for KCl. Heterodimers may form under conditions outside the above pH and salt range, medium, but some of the molecular interactions and relative stability of heterodimers vs. homodimers may differ from characteristics detailed above. For example, ionic interactions between the ionic groups that tend to stabilize heterodimers may break down at low or high pH values due to the protonation of, for example, Glu side chains at acidic pH, or the deprotonation of, for example, Lys side chains at basic pH. Such effects of low and high pH values on coiled-coil heterodimer formation may be overcome, however, by increasing salt concentration.

Increasing the salt concentration can neutralize the stabilizing ionic attractions or suppress the destabilizing ionic repulsions. Certain salts have greater efficacy at neutralizing the ionic interactions. For example, in the case of the K-coil peptide 82 in FIG. 15, a 1M or greater concentration of $ClO_4^-$ anions is required to induce maximal α-helical structure, whereas a 3M or greater concentration of $Cl^-$ ions is required for the same effect. The effects of high salt on coiled-coil formation at low and high pH also show that interhelical ionic attractions are not essential for helix formation, but rather, control whether a coiled-coil tends to form as a heterodimer vs. a homodimer.

FIGS. 14,15 show a biosensor electrode 108 in which the hydrocarbon chain monolayer 112 includes an E-coil peptide subunit, such as subunit 98, as described above. In the embodiment shown, each peptide subunit is coupled to the electrode surface via a tripeptide spacer, such as spacer 136 in subunit 98, which is itself attached to the electrode surface through a sulfhydryl linkage, as shown. The peptide, including the peptide spacer, is formed conventionally, e.g., by solid phase synthesis. The monolayer was formed according to the method described above.

Because of the negative charge imparted to the monolayer by the E-coil subunits 98, the monolayer shows relatively low conductance to negatively charged redox species, such as $Fe(CN)_6^{3-}$, as evidenced by a relatively low oxidation or reduction current with the redox species.

FIG. 15 shows the same monolayer, but after addition of complementary, positively charged K-coil subunits 82 conjugated to analyte, such as indicated at 80. As shown, oppositely charged subunits pair to form charge-neutral heterodimers in the monolayer.

Without wishing to be bound by theory, in the absence of heteroduplex formation between the two charged coiled peptides, the monolayer retains its net negative charge, forming an effective barrier to electron flow across the monolayer mediated by a redox ion species of the same charge, when a suitable oxidizing or reducing potential is placed across the monolayer. This is reflected by a low measured current across the membrane. With binding of an analyte-HSP2 conjugate to an anchored HSP1 in the monolayer, the repulsive negative of the monolayer is reduced sufficiently to allow the movement of redox species through the monolayer, producing electron flow through the electrode. The biosensor records this binding event as an increase in current across the electrode, i.e., between the working and counter electrodes. It will be recognized that the peptide used for HSP1 can have a negative or positive charge, but that the preferred redox ion has the same charge as HSP1. Thus, in an alternative embodiment of this aspect of the invention, HSP1 can be a K-coil, and a redox species of the same charge can be used, e.g., $Ru(NH_3)_6^{6+}$, with a negatively charged HSP2 used in the conjugate.

By analogy to a transistor, the redox solution serves as the "source", the monolayer as the "gate", and the underlying electrode as the "drain". Current flow in a transistor is initiated by applying a threshold voltage to the gate. In the biosensor of the invention, current flow is initiated by a stimulus—in this case, heteroduplex formation—to the monolayer "gate".

In use, the user adds three drops, or less than 100 uL of the test sample to the sample-introduction region of the diagnostic card. The sample migrates along the sample-flow pathway by capillary action and successively comes into contact with the conjugate, binding agent, and then biosensor. If the specific marker or analyte is present in the serum or plasma or other test sample, the particular analyte will mix with the conjugate. This mixture will travel by capillary action to the immobilized binding agent. The binding agent will specifically bind the analyte or conjugate. Any unbound conjugate will migrate downstream to the biosensor. The current is proportional to the concentration of analyte in the sample.

Figure 16:
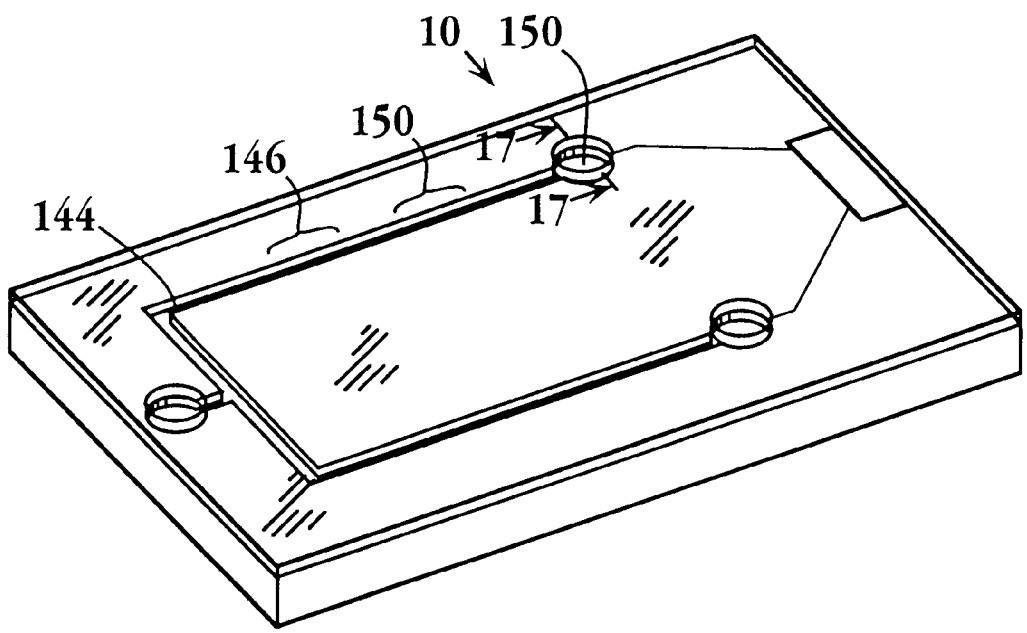
FIG. 16 is a simplified, partly schematic perspective view of an enlargement of a section of the substrate of a diagnostic device used in a Pseudomnonas PAK pilin peptide-detection showing the sample-flow pathway and biosensor in accordance with one aspect of the invention.
Figure 17:
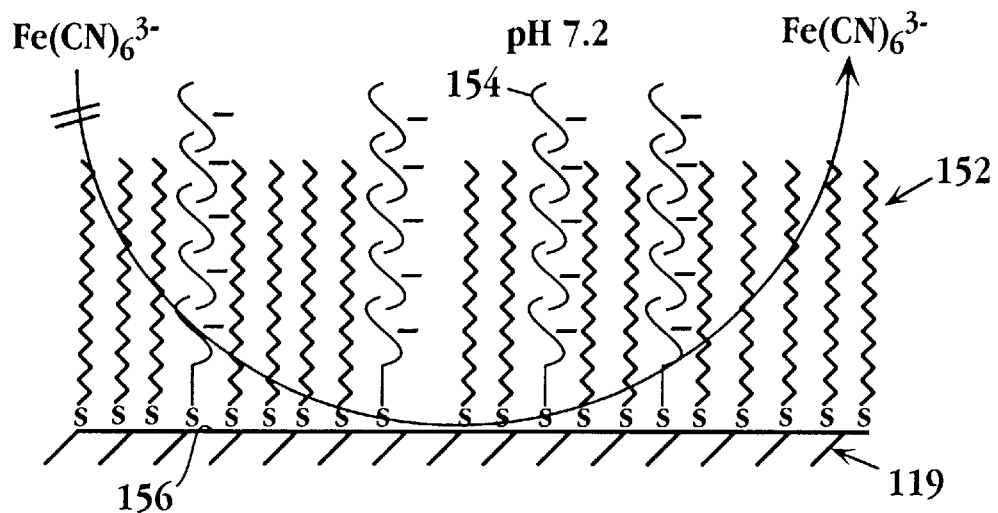
FIG. 17 is an enlarged view of a region of the electrode in the biosensor shown in FIG. 16 taken in the direction of arrows 17—17.
Figure 18:
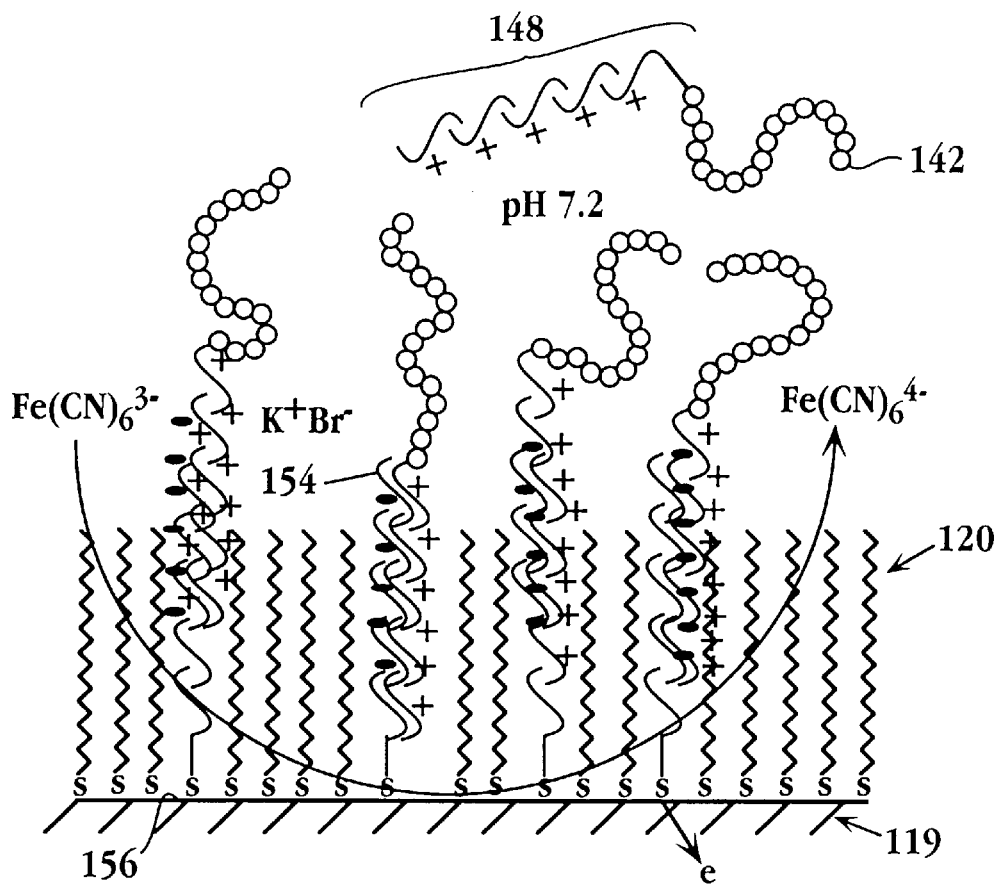
FIG. 18 is an enlarged view of a region of the electrode in the biosensor shown in FIG. 16 taken in the direction of arrows 17—17, in the presence of HSP2-PAK peptide conjugate.

FIGS. 16–18 show a diagnostic device 140 for detection and quantification of Pseudomonas PAK pilin peptide 142 constructed in accordance with the invention. The sample-flow pathway 144 of the device contains a polystyrene-divinylbenzene matrix and has a mixing zone 146 containing a conjugate 148 of HSP2-PAK peptide (HSP2 is shown at 158 and PAK peptide at 142) bound in a releasable form. Binding chamber 150 contains (16-thiohydroxy) hexadecanyl O-(2-acetamido-2-deoxy-β-D-galactopyranosyl(1→4)-D-galacopyranoside immobilized to the bibulous material through the 16 thiol moiety (not shown). This disaccharide is specifically reactive with PAK peptide, forming a ligand-receptor pair with the peptide.

FIGS. 17,18 show a magnified view of the biosensor electrode 150 of device 140 which includes a hydrocarbon monolayer 152 with embedded HSP1 154 covalently attached to the electrode surface 156. The biosensor electrode was prepared as described with reference to FIG. 14, employing a ratio of non-HSP1 to HSP1-chains of about 4 to 1. FIGS. 17 and 18 show HSP1 before and after binding of an HSP2-PAK conjugate 148, respectively.

Figure 19:
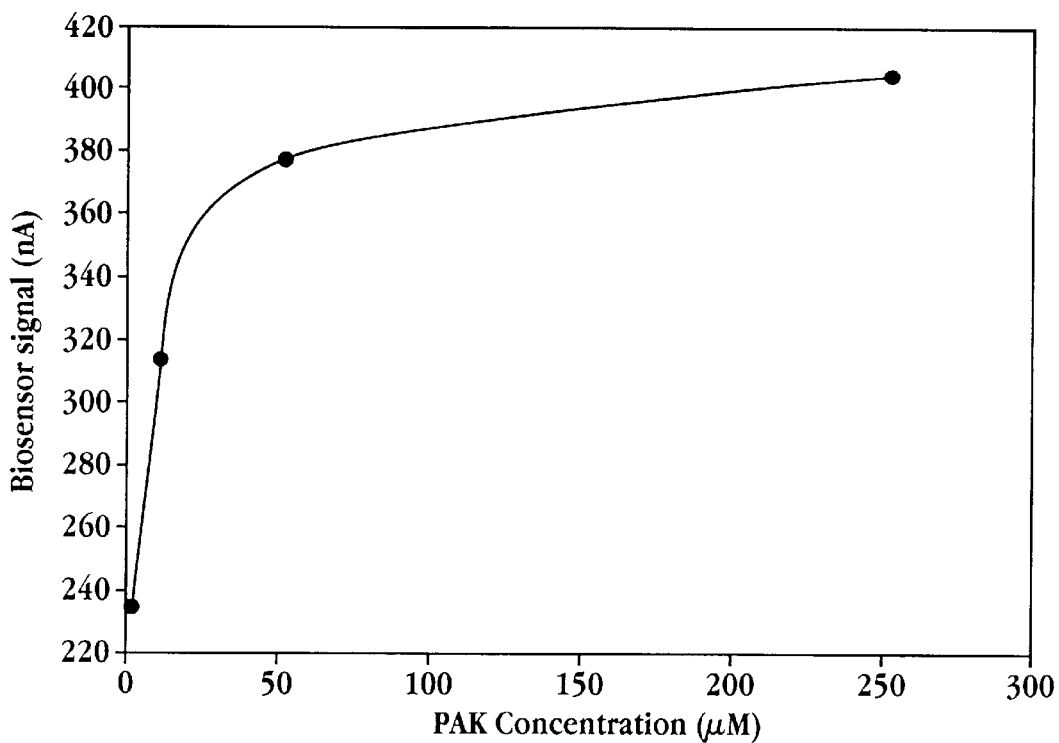
FIG. 19 is an idealized linear plot showing change in biosensor signal, measured in nA, as a function of PAK pilin peptide added to a diagnostic device of FIG. 16, where the first α-helical peptide has the same charge as the redox ion species.
Figure 20:
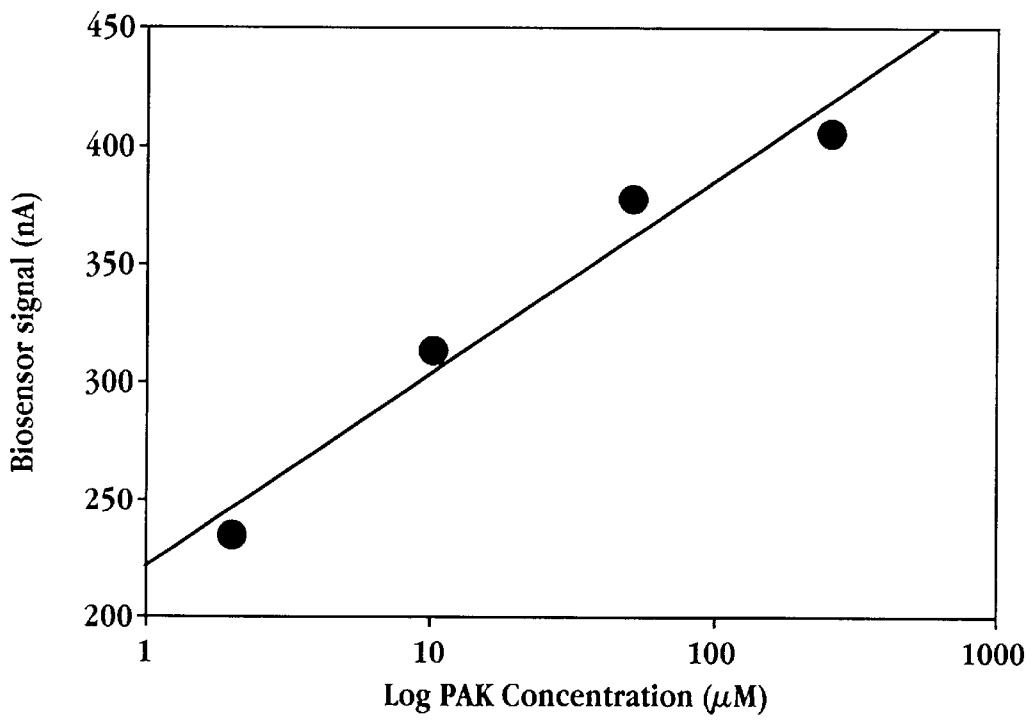
FIG. 20 is an idealized semi-log plot of the data of FIG. 19.

The operating response of the biosensor is illustrated in FIGS. 19,20. An increase in Pseudomonas PAK protein receptor in the test sample produces an increase in biosensor signal. The signal increases by about 2-fold, from 225 nA to 400 nA, over a concentration range of 0 to 250 μM PAK in the test sample.

Figure 21:
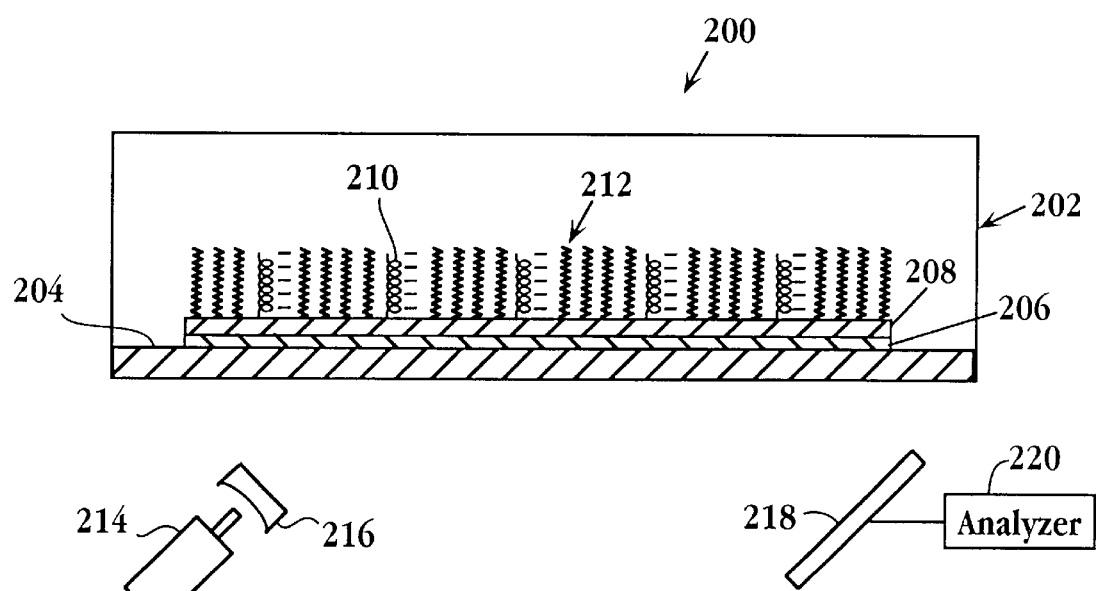
FIG. 21 shows elements of a surface plasmon resonance biosensor constructed in accordance with an embodiment of the invention.

FIG. 21 shows basic elements of a surface plasmon resonance (SPR) biosensor 200 incorporating the novel biosensor surface of the invention. A chamber 202 in the biosensor contains a waveguide composed of a dielectric film 204 (e.g., glass), a thin evaporated metal film 206 (e.g., chromium or titanium), and a thin film (preferably of gold) 208 constructed to support surface plasmon waves at the dielectric/metal film interface. The waveguide surface forms a biosensor surface having HSP1, such as E-coil peptide 210, anchored thereon. A preferred embodiment includes a hydrocarbon monolayer 212 with HSP1 peptide 210 embedded therein.

A light source 214 directs a divergent light beam onto the biosensor surface through a lens 216. At some region along the length of the biosensor surface, the beam angle strikes the surface at an absorption angle at which absorption from the evanescent wave by surface plasmons occurs. The absorption angle will shift with changes in the composition of the material near the interface, that is, in response to binding events occurring on the monolayer surface.

The intensity of reflected light from each region along the biosensor surface is monitored by a photosensor 218 whose photosensing grid is matched to specific detector surface regions, and which is operatively connected to an analyzer 220. The light source and photosensor are also referred to herein as biosensor means.

In operation, the SPR absorption angle on the biosensor surface is measured before and after application of test sample, with the measured shift in angle being proportional to the extent of surface heterodimer formation.

Figure 23:
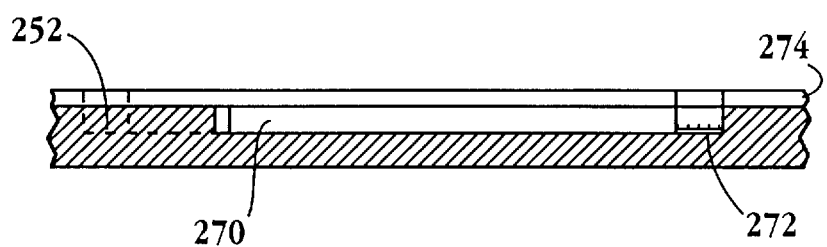
FIG. 23 is a view of a region of the device of FIG. 22 taken in the direction of arrows 23.

The detection devices described hereinabove are used in the detection of a single analyte. A multi-analyte detection device is readily constructed according to FIGS. 22 and 23 which show a multi-analyte detection device 250, and employing a biosensor selected form those as described hereinabove. The preferred device has a sample-introduction region 252, such as a port, in liquid communication with each of a plurality of sample-flow pathways, such as flow paths 254,256. Each sample-flow pathway has a separate mixing zone, binding zone, and biosensor for measuring a different analyte present in the test sample. Each mixing zone, such as 258, 260, contains a separate, releasably bound HSP2-analyte (or analyte analog) conjugate for each analyte being detected. Each binding zone, such as 262, 264, contains an immobilized analyte-binding agent corresponding to the HSP2-analyte conjugate in the associated mixing zone. In one embodiment, all of the biosensors, such as at 266, 268, 272 contain HSP1 anchored to an electrochemical detection surface within a hydrocarbon monolayer as described hereinabove. In a preferred multi-analyte device, at least one of the sample-flow pathways, such as 270, is a control sample-flow pathway which lacks analyte/HSP2 conjugate. In the operation of this embodiment of the invention, test sample applied to the sample application region 252 flows into each of the separate sample-flow pathways and interacts with the respective reagents within each sample-flow pathway in analogy to the dual lane electrochemical device illustrated in FIG. 7. Each biosensor is connected to a detector for measuring the change in signal generated by each biosensor, in response to heteroduplex formation. The device preferably is provided with a lid 274.

The device preferably includes at least one biosensor which will be used as a positive control biosensor. This biosensor is not connected to the sample application port. It includes a fixed amount of HSP2-analyte conjugate pre-added, during manufacture of the positive control biosensor chamber, in an amount to give the limit of maximum expected response. Preferably, the positive control biosensor chamber contains the HSP2/analyte conjugate, redox species probe, and buffer-salts in a dried form which are rehydrated at the time of use of the device. For example, an aliquot of aqueous solution (e.g., albumin) can be contained in a reservoir (not shown). The control solution can be injected into the positive control biosensor chamber through a passage between the chamber and reservoir. The injection can be performed electronically, e.g., by a minipump or electroomotic movement of solution through the passage, or manually, e.g., by depressing an injection means such as a flexible bulb associated with the reservoir (not shown).

Figure 24:
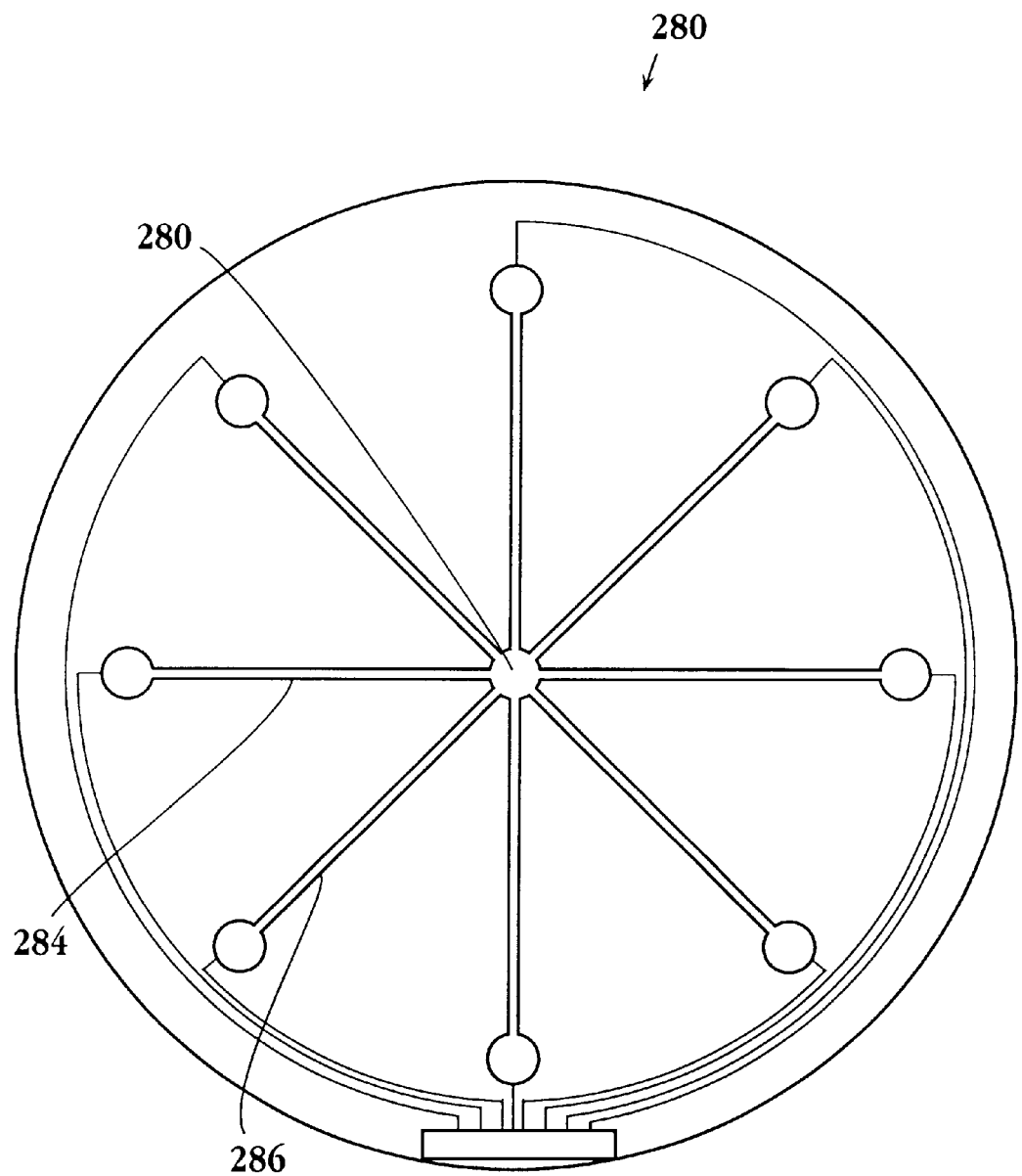
FIG. 24 is a simplified, partly schematic view of the top side of a multi-analyte detection device in accordance with one aspect of the invention.

Another embodiment of a multi-analyte detector is a circular device 280 (FIG. 24) having a sample-introduction region 282, such as a port, in liquid communication with each of a plurality of sample-flow pathways, such as flow paths 284, 286. Each sample-flow pathway has a separate mixing zone, binding zone, and biosensor for measuring a different analyte present in the test sample in analogy with the device 250 as described hereinabove. When placed in a reader (not shown), each biosensor can be rotatably positioned for detection, such as by the stationary light source and photosensor of an SPR detector (not shown). Simultaneously, the electrical current of each biosensor can be detected as described hereinabove.

From the foregoing, it can be seen how various objects and advantages of the invention are met. The biosensor of the diagnostic card can be formed under controlled manufacturing conditions consistent with microchip scale and photomask processes, to produce highly uniform and/or miniaturized and/or high-density array biosensor devices with sample-introduction region, biosensor, and sample-flow pathway microfabricated on the substrate. The invention can incorporate multi-analyte assay surfaces by photomasking techniques that are capable of producing diagnostic devices having a plurality of unique sample-flow pathways, in fluid communication with highly reproducible biosensor elements.

After manufacture of a device with a plurality of identical biosensors, the plurality of sample-flow pathways can be readily adapted to a wide variety of analytes(s), by binding an HSP2 peptide conjugate in a releasable form within the mixing zone and by binding analyte-binding agent in an immobilized form within the binding zone, carried out under relatively simple production conditions, thus combining both manufacturing precision at the initial production stage, and assay flexibility at the analyte and analyte-binding agent addition stage.

Figure 25:
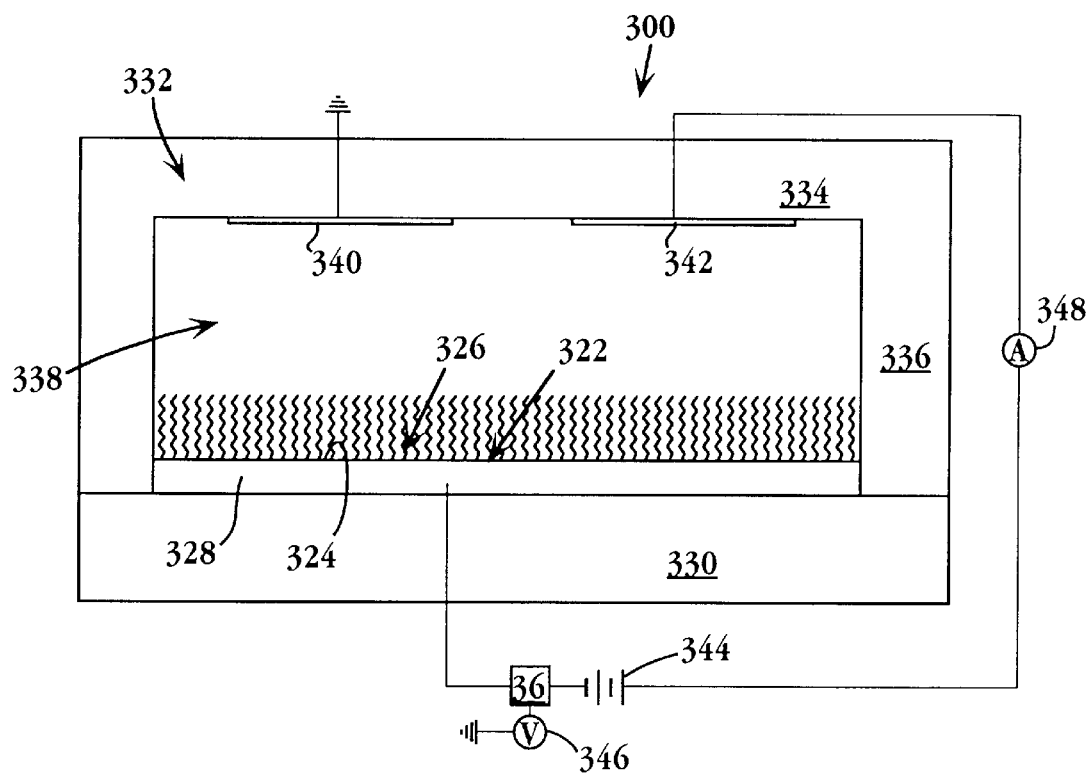
FIG. 25 is a simplified, partly schematic view of a biosensor constructed in accordance with an embodiment of a diagnostic device of the invention.

In another embodiment of the invention, FIG. 25 is a simplified schematic view of a biosensor 300 for detecting a binding event between an analyte and an analyte-binding agent. The apparatus includes a working electrode 322 having a conductive detection surface 324, and a hydrocarbon-chain monolayer 326 formed on the detection surface. In the embodiment shown, the detection surface is the upper surface of a conductive film 328 deposited on an electrode substrate 330, which may be non-conductive material. Details of the monolayer formed on the detection surface, and the method of forming the monolayer on the surface, are discussed below. Biosensor 300 is adapted to be used in card 10 (FIGS. 1–7) having a sample-introduction region and sample-flow pathways (in analogy to FIG. 8A), however, in this embodiment, the sample-flow pathway preferably lacks bibulous material, conjugate, and analyte-binding agent. Thus, the liquid sample flows directly to the biosensor 300 for analysis from the sample-introduction region.

A cover 332 in the apparatus has an upper wall 334, and side walls, such as wall 336, which are joined to edge regions of the electrode substrate to form a closed chamber 338 therewith. In analogy with device 100, the chamber serves to hold a liquid test sample in an aqueous electrolyte solution required for biosensor operation, as will be described.

The other elements of the biosensor are analogous to those of device 100 and include reference electrode 340 and counter electrode 342 in the apparatus are carried on the chamber-facing surface of wall 334; voltage source 344; and current measuring device 348.

Figure 26:
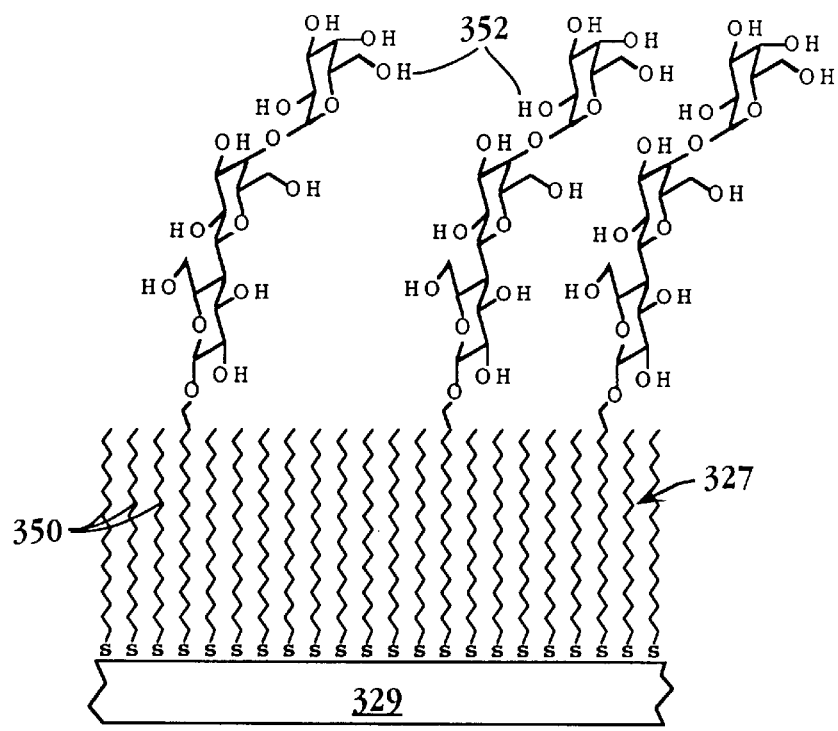
FIG. 26 is an enlarged view of a region of the electrode in the biosensor shown in FIG. 25.

FIG. 26 is an enlarged view of a portion of the working electrode for use in a biosensor such as at 300 with conductive film 329 and including the electrode monolayer, showing individual hydrocarbon chains, such as chains 350, forming the monolayer 327, and analyte binding molecules, such as trisaccharide molecules 352, covalently attached to distal ends of the hydrocarbon chains.

The analyte-binding agents are attached to distal ends of the chains through conventional derivatization reactions, e.g., ester, ether, amide, or sulfhydryl linkages, according to standard methods. The number of chains in the monolayer carrying distal-end analyte-binding agent is preferably about 1 to 10 mole percent of the total chains, but may range from 0.01 to 100%.

The chains forming the monolayer are typically 8–22 carbon, saturated hydrocarbon chains, although longer chains, chains with some unsaturation, chains with non-carbon chain atoms, such as lipid ethers, and/or chains with minor branching, such as by non-chain methyl groups, may be employed, within the constraint that the chains, at a sufficient packing density, form a sufficiently close packed and ordered monolayer to be effective as a barrier to electron flow, under biosensor operating conditions, as discussed below. This density is calculated to be between 3–5 chains/nm$^2$.

Figure 45:
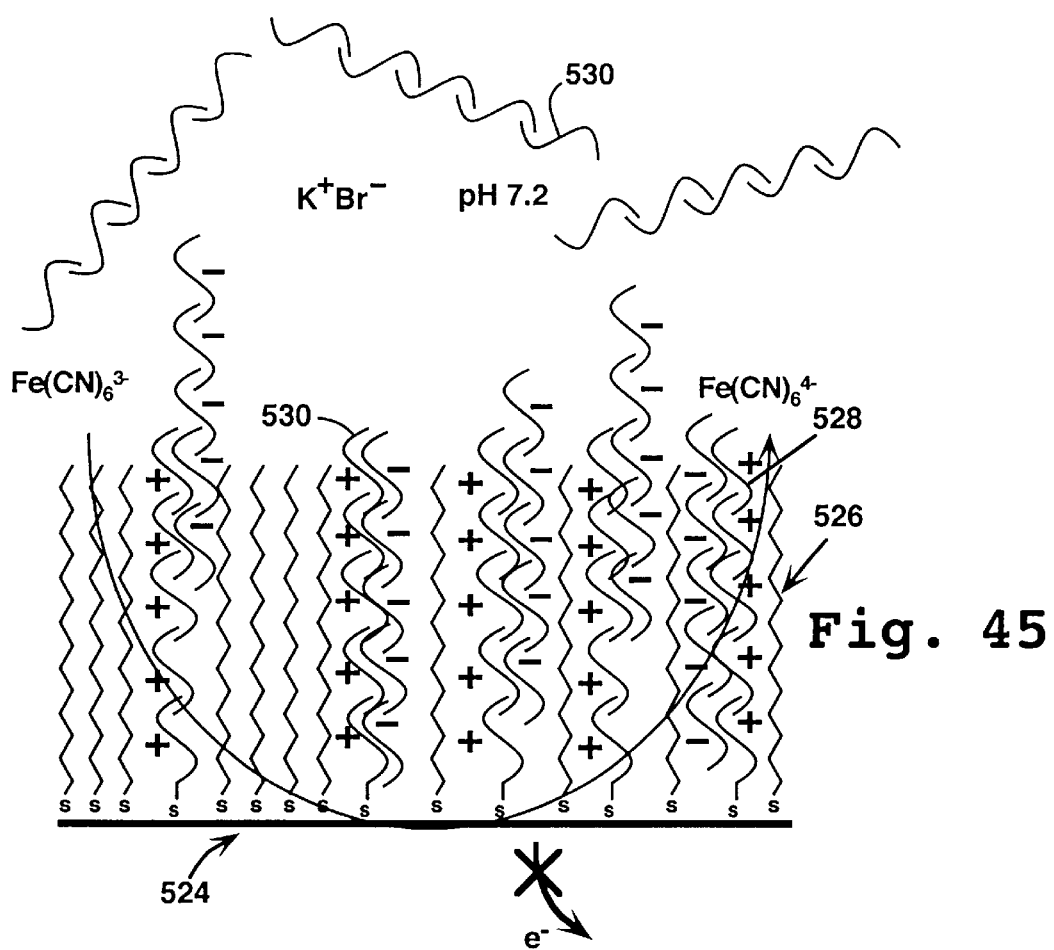
FIG. 45 illustrates the structure of an electrode monolayer having an embedded K-coil peptide subunit, and an embedded K-coil/E-coil heteroduplex.

As an example of the variation in chain composition allowed, the embodiment of the invention shown in FIG. 45 has a hydrocarbon-chain monolayer that includes coil-coil peptide heterodimers embedded in the planar chain matrix, while still retaining a low dielectric barrier to ion flow through the monolayer.

In the embodiment shown (FIG. 26), the chains are coupled to the electrode detecting surface through sulfhydryl linkages, although other suitable coupling groups may be employed. Methods for producing monolayers having suitable hydrocarbon chain densities will now be discussed.

FIGS. 27–29 illustrate three methods for forming hydrocarbon chain monolayers suitable for use in the biosensor electrodes.

One approach, illustrated in FIG. 27, involves passive diffusion of chains, such as hydrocarbon chains 354 and analyte-binding agent-derivatized chains, such as chains 356, onto the surface of electrode 358, under conditions effective to couple the diffused chains to the electrode detection surface. The diffusion method illustrated in FIG. 27 is a two-step process. In the first step, hydrocarbon chains alone (in the absence of analyte-binding agent-derivatized chains) are allowed to react with the detected surface over an extended period, e.g., 24–48 hours, until a selected packing density less than full packing density is achieved.

The diffusion reaction is carried out under conditions suitable for coupling the derivatized chains to the detection surface. Where the chains have thiol coupling groups, and the electrode surface is gold, the surface is subjected to mild electro-chemically oxidizing conditions, with a perchlorate salt present in solution, then reacted with the chains under mildly oxidizing conditions.

The extent of packing can be monitored, for example, by ellipsometry measurements to determine the thickness of the layer on the detection surface. At maximum density, i.e., saturation, a given chain length will produce a given monolayer thickness. As a guide, $C_{22}$ chains produce a maximum monolayer thickness of about 30 Å, and shorter length chains, proportionately thinner monolayers. Thus, in the case of a monolayer formed of $C_{22}$ chains, the passive buildup of the monolayer may be stopped when a 25 Å monolayer thickness is observed.

The second diffusion step involves the passive diffusion of analyte-binding agent-derivatized thiol-chains 356 onto the partially formed monolayer, indicated at 360, again under suitable thiolate coupling conditions, until a high-density monolayer 362 is achieved, as evidenced, for example, by the measured thickness of the monolayer and/or a plateauing of the thickness/time curve.

Although this approach has been applied successfully to monolayer production in the invention, it suffers from two limitations. First, rather long diffusion times—on the order of one to several days—are required to reach maximum packing density. Secondly, the percent chains containing attached analyte-binding agent is difficult to control reproducibly, so that the final monolayers will have variable mole percentages of analyte-binding agent molecules, and thus, different performance characteristics.

These limitations are substantially overcome in the method illustrated in FIG. 28, in accordance with another novel aspect of the invention. In this approach, a mixture of free and analyte-binding agent-carrying hydrocarbon chains, such as chains 366, 368, respectively, at a desired mole ratio, are actively driven to the surface by applying a positive voltage potential to the substrate, here indicated at 364. In practice, the hydrocarbon chain mixture (about 1 mM hydrocarbon chains) in an ethanolic solution of 100 mM Li perchlorate, neutral pH, is added placed over the electrode, and a selected potential is applied to the electrode. The buildup of the monolayer can be monitored by increase in layer thickness, as above. Preferably, however, monolayer formation is monitored by measuring electron flow across the monolayer, e.g., employing the circuit configuration shown in FIG. 25. In this case, formation of the monolayer, indicated at 370, will be characterized by a steady drop in electrode current, until a stable low current flow is reached, at which point maximum chain packing has been achieved.

Figure 30:
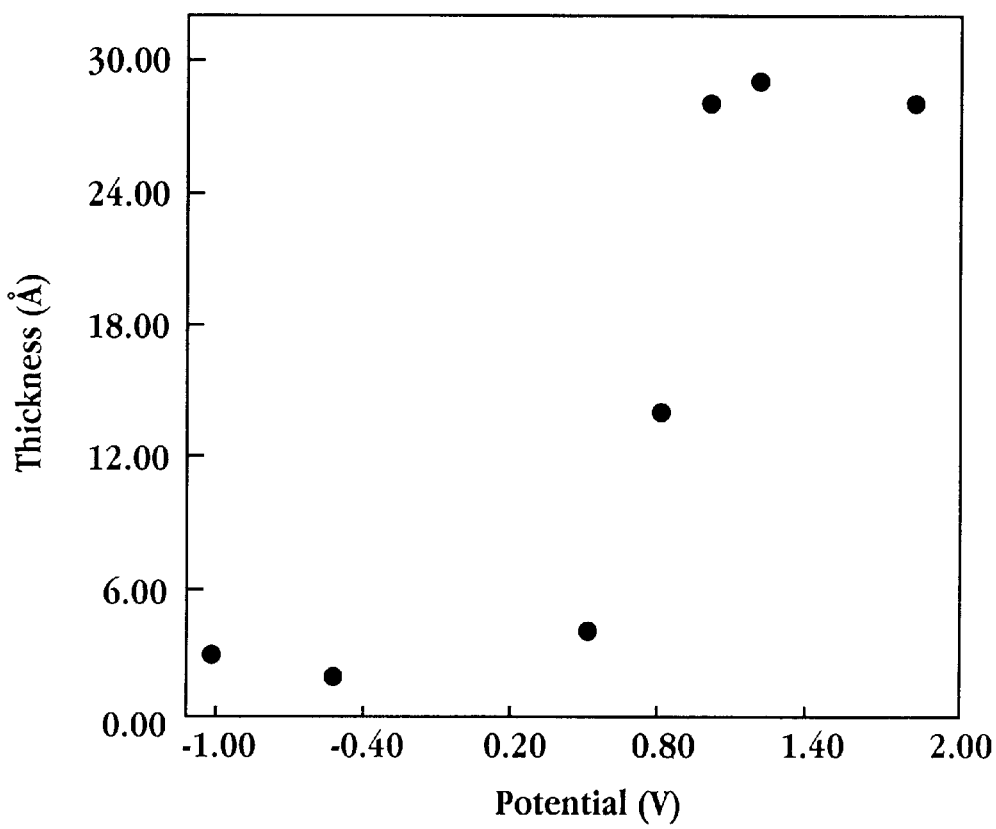
FIG. 30. is a plot of monolayer thickness as a function of applied voltage in an electrode monolayer formed in accordance with the method illustrated in FIG. 28.

The time required to achieve saturation packing density will vary with applied voltage, and can be a short as 10 seconds—that is, about 4 orders of magnitude faster than monolayer formation by diffusion. FIG. 30 is a plot of monolayer thickness formed using a thiol-group $C_{22}$ hydrocarbon chain under coupling conditions like those above, after 10 minutes at the electrode voltage indicated. As seen, complete or nearly complete monolayer formation (30 Å thickness) occurs within 10 minutes at about 1V (vs. NHE) potential and above. At lower positive voltages, additional reaction time is required. Preferably the voltage applied to the electrode is at least voltage between about +250 mV relative to a normal hydrogen electrode (+250 vs. NHE) and 1.2V (vs. NHE).

Not only are rapid monolayer formation times achieved, but the percentages of analyte-binding agent- and non-analyte-binding agent chains present in the reaction mixture are precisely represented in the monolayers, giving highly reproducible electrode characteristics.

FIG. 29 shows a modification of the FIG. 28 method, where the hydrocarbon-chain mixture reacted with the electrode (indicated at 371) includes non-analyte-binding agent chains, such as chains 372, and peptide subunit conjugates, such as indicated at 374, containing a peptide subunit 376 (e.g., K-coil) that is capable of forming a stabilized, alpha-helical peptide heterodimer with an oppositely charged, complementary subunit (e.g., E-coil).

In the embodiment shown, subunit 376 is attached to the distal end of a hydrocarbon chain 378 (end opposite the chain's thiol group) by suitable lipid-to-peptide conjugation, e.g., by ester linkage to a hydrocarbon fatty acid. Alternatively, and as described below, the peptide subunit may be linked to the electrode surface through a peptide spacer, e.g., tripeptide spacer that extends from one end of the subunit and includes cysteine as a terminal residue, for sulfhydryl attachment to the electrode surface. In both cases, the peptide subunit conjugate is mixed with the hydrocarbon chains, at a selected mole ratio, then driven into a monolayer formation by applying a positive voltage to the electrode, as above, until a densely packed monolayer 380 is formed.

A suitable analyte-binding agent is then attached to the monolayer by contacting the monolayer with an analyte-binding agent-coil conjugate 382 composed of the oppositely charged complement of the monolayer coil, indicated at 384, coupled to a selected analyte-binding agent 386. The two oppositely charged subunits spontaneously self-assemble into heterodimers, effectively coupling the analyte-binding agent to the monolayers with the high affinity constant of the two heterodimers.

The method provides, in addition to the advantages mentioned above with respect to FIG. 28, a "universal" biosensor substrate which can be modified to include one of a large number of different analyte-binding agents in the substrate monolayer simply by contacting the universal substrate with a conjugate of the oppositely charged peptide subunit and the selected analyte-binding agent. In the example shown in FIG. 29, a universal substrate monolayer 380 is converted to an analyte-specific monolayer 388 by addition of the analyte-specific conjugate 382.

The following discussion examines the dielectric properties of the biosensors of the present invention, as evidenced by the conductance properties of the biosensor monolayer membranes in the presence and absence of analyte/analyte-binding agent binding. The discussion considers membranes having directly attached analyte-binding agent of the type described with respect to FIGS. 27 and 28. A following discussion examines similar electrical properties in biosensor membranes in which the analyte-binding agent is attached through heterodimer peptide subunits, as described with respect to FIG. 29.

Figure 31:
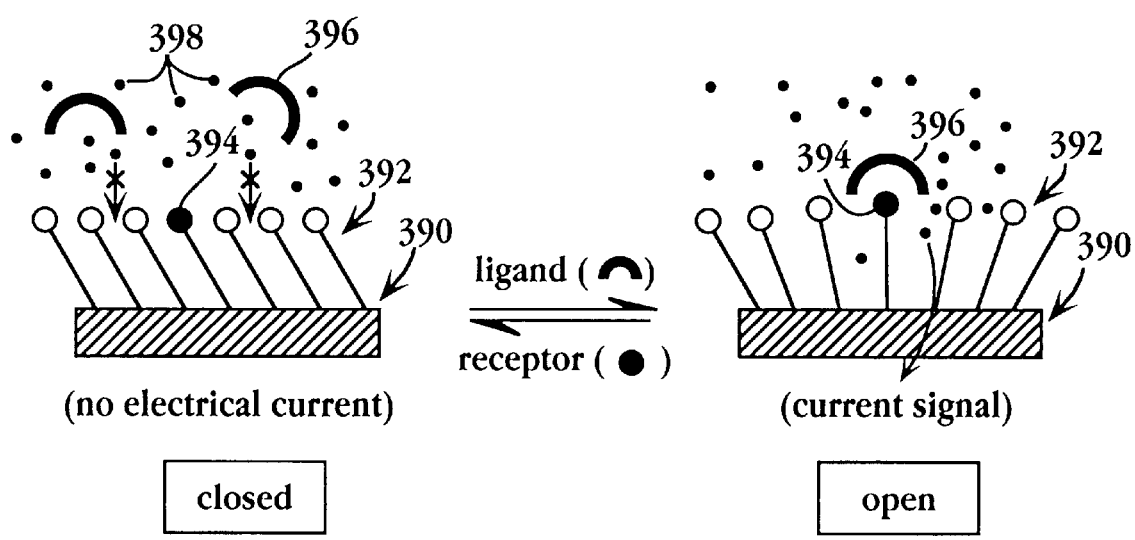
FIG. 31 illustrates the triggering of conductance by receptor-ligand interaction on a biosensor electrode, in accordance with a biosensor used in the device of the invention.

The basic operational features of an embodiment of a biosensor of the invention are illustrated in FIG. 31. The figure shows a biosensor electrode 390 in a biosensor apparatus of the type described in FIG. 25, where an electrode monolayer 392 is formed, as above, of a densely ordered array of hydrocarbon chains containing analyte-binding agent molecules, such as molecule 394, attached to the distal ends of some of the chains.

The electrode is in contact with a solution of ionic species, indicated at 398, capable of undergoing a redox reaction, i.e., losing or gaining an electron, at a suitably charged electrode. Typical redox ion concentrations are between 0.01 and 10 mM. The redox solution is contained in chamber, like chamber 338 (FIG. 25), and is in contact with reference and counter electrodes.

The voltage potential placed on the electrode, i.e., between the electrode and reference electrode, is typically at least 90 mV above the electrochemical potential ($e_0$) value of the redox species, for oxidation, and at least 90 mV below the electrochemical potential, for reduction of the species.

In the absence of analyte binding to the analyte-binding agent, the monolayer retains its dense ordered packing, forming an effective barrier to electron flow across the monolayer mediated by the redox ion species, when a suitable oxidizing or reducing potential is placed across the monolayer. This is reflected by a low or zero measured current across the membrane. The dielectric constant of the monolayer in this condition is typically about 1–2.

With binding of an analyte 396 to an analyte-binding agent on a monolayer, as shown at the right in FIG. 31, the ordered structure of the monolayer is perturbed sufficiently to allow the movement of redox species through the monolayer, producing electron flow through the electrode. Measurements performed in support of the invention indicate that one triggering event leads to $10^2$ to $10^6$ ionic and electron transfer events per second, and thus is highly multiplicative. The biosensor records this binding event as an increase in current across the electrode, i.e., between the working and counter electrodes.

By analogy to a transistor, the redox solution serves as the "source", the monolayer as the "gate", and the underlying electrode as the "drain". Current flow in a transistor is initiated by applying a threshold voltage to the gate. In the biosensor of the invention, current flow is initiated by a stimulus—in this case, an analyte/analyte-binding agent binding event—to the monolayer "gate".

A biosensor electrode 400 constructed in accordance with the invention, and having a disaccharide analyte-binding agent indicated at 402 is shown before and after analyte binding in FIGS. 32 and 33, respectively. Synthesis of the disaccharide-hydrocarbon chain used in the membrane is described in Examples 1D and 1E. The electrode was prepared as described with reference to FIG. 28, employing a ratio of non-analyte-binding agent to analyte-binding agent chains of about 4 to 1. The disaccharide is specifically reactive with a Pseudomonas PAK peptide, indicated at 404, forming an analyte/analyte-binding agent pair with the peptide.

Figures 32, 33:
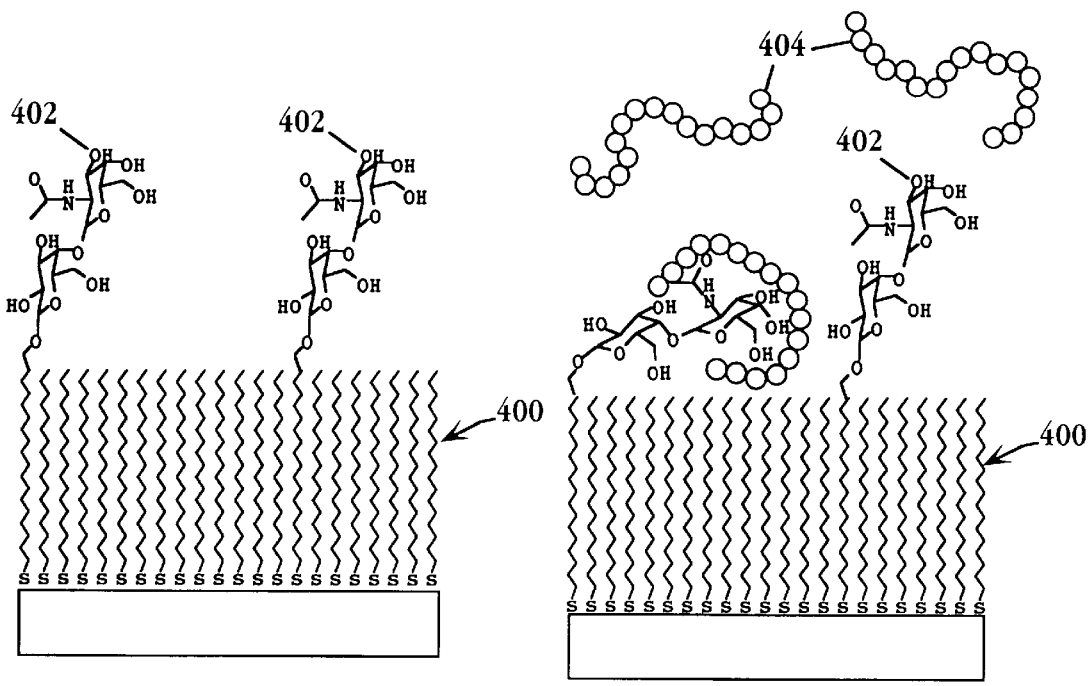
FIG. 32 illustrates a biosensor having disaccharide ligands bound on a lipid monolayer.
FIG. 33 illustrates the perturbation of the lipid monolayer structure with binding of PAK peptide to disaccharide ligands on a monolayer of FIG. 32.
Figure 34:
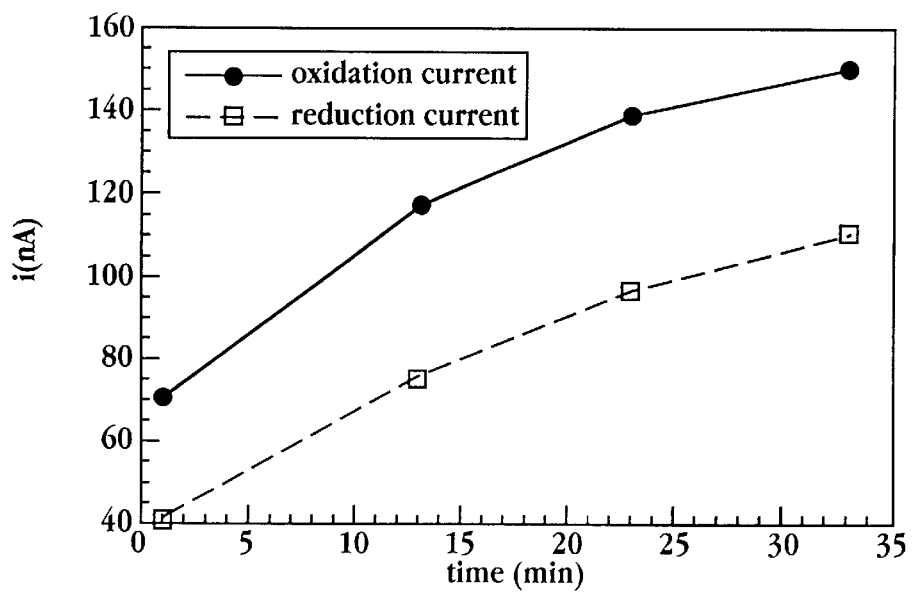
FIG. 34 shows plots of changes in oxidation (solid circles) and reduction (open squares) current of $Fe(CN)_6^{3-/4-}$ as a function of time after addition of PAK peptide to the monolayer illustrated in FIG. 32.

The increase in biosensor electrode current, when PAK peptide receptor is added to the biosensor chamber, is seen in FIG. 34 for both oxidation (solid circles) and reduction (open squares) current from $Fe(CN)_6^{3-/4-}$. The increase over time presumably reflects the kinetics of binding, demonstrating that the biosensor is useful as well in measuring the rate of analyte/analyte-binding agent binding events. FIG. 33 illustrates the perturbation of the hydrocarbon chain structure with analyte binding.

Figure 35:
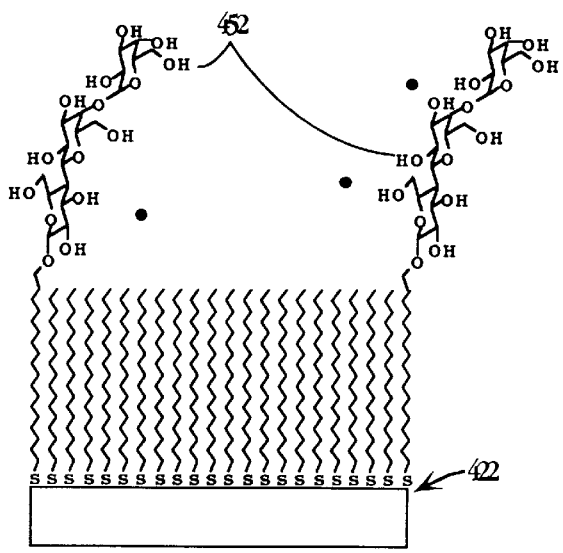
FIG. 35 illustrates a biosensor having trisaccharide ligands bound on a lipid monolayer.

As another example, the biosensor electrode illustrated in FIGS. 35–37 (electrode 422) has a trisaccharide ligand 452 which is shown before and after analyte binding in FIG. 35 and FIGS. 36 and 37, respectively. Synthesis of the trisaccharide-hydrocarbon chain used in the membrane is described in Examples 1B and 1C. The electrode was prepared as described with reference to FIG. 28, employing a ratio of non-modified to modified-chains of about 4 to 1. The disaccharide is specifically reactive with Verotoxin, indicated at 106, forming an analyte/analyte-binding agent pair. Verotoxin was prepared as described in Example 2.

Figures 36, 37:
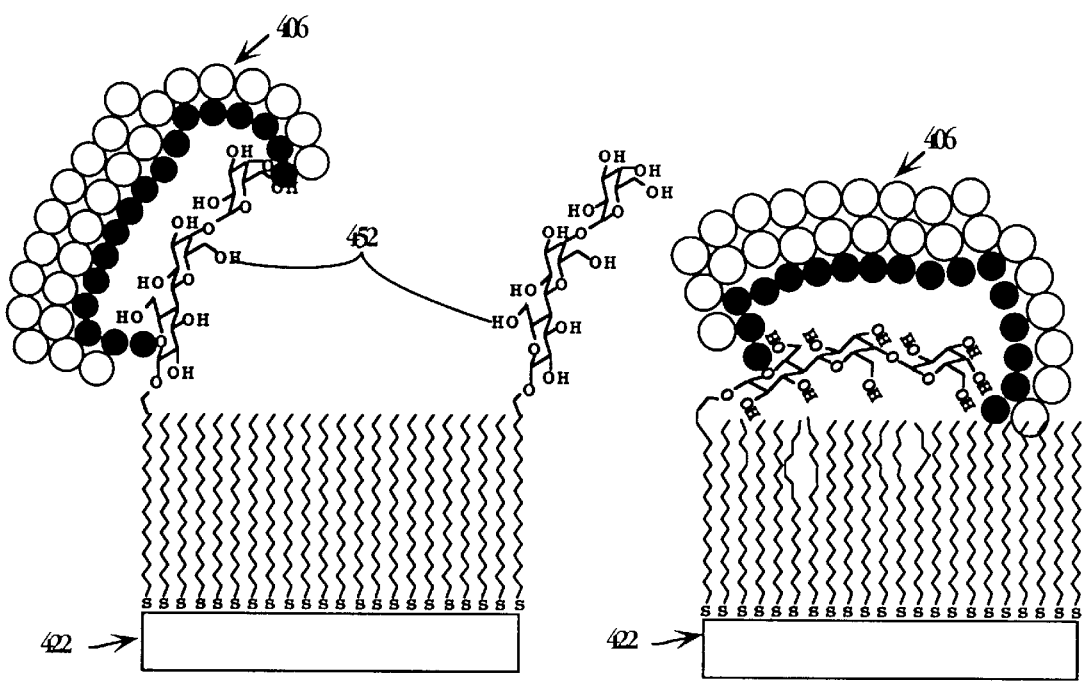
FIG. 36 illustrates binding of Verotoxin to a lipid monolayer of FIG. 35.
FIG. 37 illustrates the perturbation of lipid monolayer structure with binding of Verotoxin to trisaccharide ligands on a monolayer of FIG. 35.

FIGS. 36 and 37 illustrate two possible binding configurations. The configuration in FIG. 36 has little effect on the monolayer structure, and hence on biosensor current, because binding is "remote" from the membrane surface; the configuration illustrated in FIG. 37, by contrast, produces significant perturbation of the monolayer structure, and thus would be expected to significantly enhance biosensor current.

Figure 38:
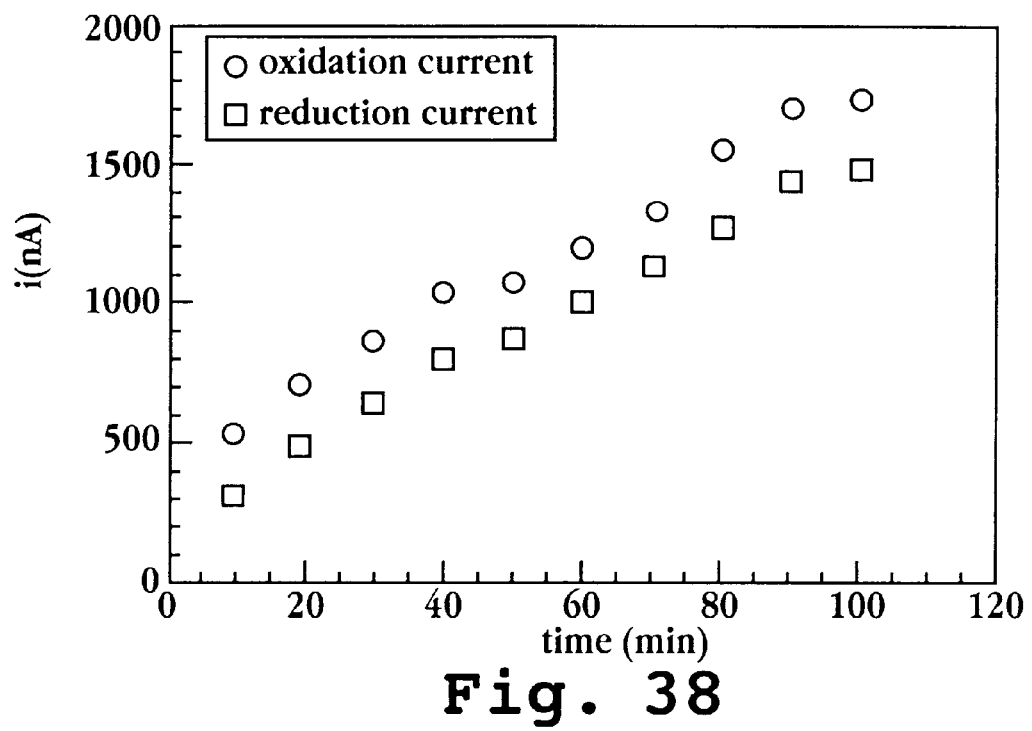
FIG. 38 shows plots of changes in oxidation (solid circles) and reduction (open squares) current of $Fe(CN)_6^{3-/4-}$ as a function of time after addition of Verotoxin to the monolayer illustrated in FIGS. 35–37.

The oxidation and reduction current plots shown in FIG. 38 demonstrate that Verotoxin binding to the membrane does in fact produce a major change in monolayer structure. As seen, both oxidation and reduction current increase from near-zero levels, in the absence of Verotoxin, to a level in the $\mu$Amp range an hour after Verotoxin is introduced into the biosensor.

In the examples above, the stimulation of biosensor current by analyte binding may be the result of (i) steric perturbation of the monolayer chains, as indicated in FIGS. 33 and 37, (ii) charge effects on the monolayer surface due to charged groups on the receptor, or (iii) a combination of the both effects. Studies conducted in support of the invention indicate that both effects can be operative.

Figure 39:
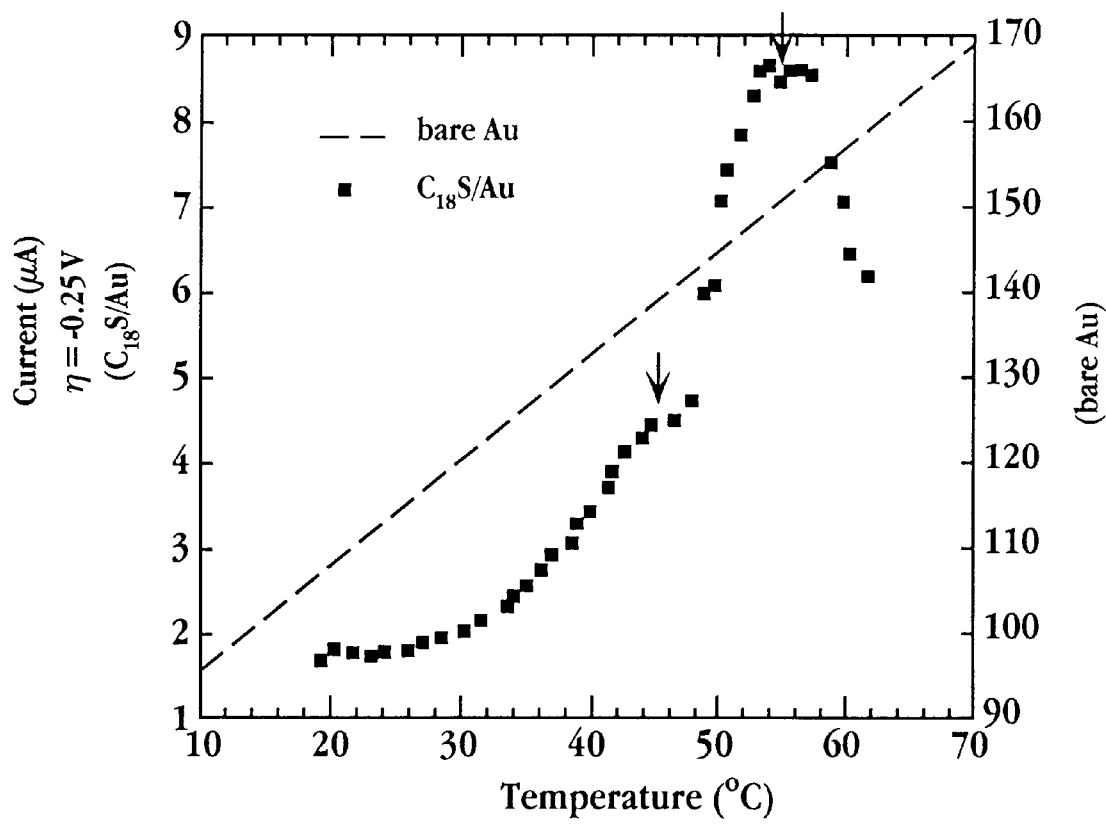
FIG. 39 is a plot of electrode current of $Fe(CN)_6^{3-/4-}$ as a function of temperature in a monolayer electrode constructed in accordance with the invention.

The effect of hydrocarbon-chain disruption in the biosensor monolayer, was examined by plotting biosensor current as a function of electrode temperature. If lipid-chain disruption leads to greater electron flow in the biosensor, raising the temperature of the monolayer, and thus the motion of the lipid chains, should increase measured electron flow mediated by redox carriers. This was in fact observed, as seen in FIG. 39. The current/temperature plot has a peak corresponding to the phase transition temperature of the monolayer chains (about 55° C.), consistent with the idea that maximum lipid disruption occurs at the point of maximum extent of phase boundaries in the hydrocarbon chains.

The effect on conductance of charge on the monolayer surface can be seen from FIGS. 41 and 43. In the study represented in FIG. 40, a negatively charged analyte-binding agent was attached to the distal ends of a portion of the chains forming the monolayer. In the figure, the electrode is indicated at 508, the monolayer, at 510, chains forming the monolayer, at 512, and chain-attached analyte-binding agent, at 514. Electrode current was measured for the negatively charged redox species $Fe(CN)_6^{3-/4-}$, and independently, with the positively charged species $Ru(NH_3)_6^{2+/3+}$, at oxidation potentials indicated above.

As seen in FIG. 41, the oxidation current for the positively charged species shows the ion-dependent behavior expected for ion migration through the monolayer, indicating that the monolayer is conductive to positively charged redox species. Conversely, no significant electron flow was observed with the negatively charged redox species.

Similar results were obtained with a monolayer designed to contain a positively charged surface analyte-binding agent, as illustrated in FIG. 42. In this figure, the electrode is indicated at 516, the monolayer, at 518, chains forming the monolayer, at 520, and chain-attached analyte-binding agent, at 522. In this case, ion-dependent current was observed for oxidation of the negatively charged iron redox species, but not the positively charged ruthenium species (FIG. 43).

In another embodiment of the biosensor, the analyte-binding agent in the biosensor is anchored to biosensor surface, i.e., embedded within the hydrocarbon-chain monolayer, by a coiled-coil heterodimer complex formed of two subunit peptides. The heterodimer-subunit peptides employed in the biosensor invention are two non-identical, preferably oppositely charged polypeptide chains, typically each about 21 to about 70 residues in length, having an amino acid sequence compatible with their formation into two-stranded α-helical heterodimeric coiled-coils as described hereinabove as HSP1 and HSP2. In the discussion related to this embodiment, HSP1 will refer to the peptide attached to the biosensor surface in the biosensor, and HSP2, to the peptide having an attached analyte-binding agent. It will be understood that these designations refer to the functional role played by the subunit peptide, not the actual peptide sequence.

As just noted, one of the two subunit peptides (HSP1) in the heterodimer is attached to the biosensor surface, and the second peptide (HSP2) contains an analyte-binding agent intended to participate in an analyte-dependent analyte/analyte-binding agent binding reaction. In both cases, the peptide is synthesized, or derivatized after synthesis, to provide the requisite attachment function and analyte-binding agent, respectively.

Considering the modification of HSP1, the peptide may be synthesized, at either its N or C terminus, to carry additional terminal peptides that can function as a spacer between the biosensor surface and the helical-forming part of the peptide. Alternatively, the HSP1 peptide can be attached to the biosensor surface thorough a high-affinity binding reaction, such as between a biotin moiety carried on the peptide and an avidin molecule covalently attached to the surface.

Where the heterodimer is embedded in a hydrocarbon-chain monolayer, as described below, the spacer anchoring the HSP1 peptide to the biosensor surface may be a hydrocarbon chain. The chain is preferably a fractional length of the chains making up the bilayer, such that the distal ends of the heterodimer peptides in the assembled monolayer are at or near the exposed surface of the monolayer. Thus, for example, if the monolayer is made up of 18-carbon chains, the spacer is preferably 2–10 carbons in length, depending on the length of the assembled heterodimer.

The hydrocarbon-chain spacer, in the form of a omega-thio fatty acid, may be coupled to a terminal hydroxyl or amine coupling during solid-phase synthesis, as outlined above. The derivatized peptide, in turn, can be attached to a metal surface by standard thiolate coupling.

Where the analyte-binding agent is a polypeptide, e.g., peptide antigen, the antigen can be synthesized by either solid-state or recombinant methods, to include the peptide antigen at the end of the HSP2 peptide that will orient distally in the assembled heterodimer. Where the analyte-binding agent is a non-peptide moiety, e.g., a non-peptide hormone, drug, or nucleic acid, the HSP2 peptide can be synthesized to include one or more residues that can be specifically derivatized with the analyte-binding agent. The analyte-binding agent is preferably covalently attached to the N-terminal amino acid residue, or to one or the residues facing the exposed face of the heterodimer. Preferred coupling groups are the thiol groups of cysteine residues, which are easily modified by standard methods. Other useful coupling groups include the thioester of methionine, the imidazolyl group of histidine, the guanidinyl group of arginine, the phenolic group of tyrosine and the indolyl group of tryptophan. These coupling groups can be derivatized using reaction conditions known to those skilled in the art.

To attach the analyte-binding agent-derivatized HSP2 peptide to the surface-immobilized HSP1 peptide, the two peptides are contacted under conditions that favor heterodimer formation. A medium favoring coiled-coil heterodimer formation is a physiologically-compatible aqueous solution typically having a pH of between about 6 and about 8 and a salt concentration of between about 50 mM and about 500 mM. Preferably, the salt concentration is between about 100 mM and about 200 mM. An exemplary benign medium has the following composition: 50 mM potassium phosphate, 100 mM KCl, pH 7. Equally effective media may be made by substituting, for example, sodium phosphate for potassium phosphate and/or NaCl for KCl. Heterodimers may form under conditions outside the above pH and salt range, medium, but some of the molecular interactions and relative stability of heterodimers vs. homodimers may differ from characteristics detailed above. For example, ionic interactions between the ionic groups that tend to stabilize heterodimers may break down at low or high pH values due to the protonation of, for example, Glu side chains at acidic pH, or the deprotonation of, for example, Lys side chains at basic pH. Such effects of low and high pH values on coiled-coil heterodimer formation may be overcome, however, by increasing salt concentration.

Increasing the salt concentration can neutralize the stabilizing ionic attractions or suppress the destabilizing ionic repulsions. Certain salts have greater efficacy at neutralizing the ionic interactions. For example, in the case of the K-coil peptide, a 1M or greater concentration of $ClO_4^-$ anions is required to induce maximal α-helical structure, whereas a 3M or greater concentration of $Cl^-$ ions is required for the same effect. The effects of high salt on coiled-coil formation at low and high pH also show that interhelical ionic attractions are not essential for helix formation, but rather, control whether a coiled-coil tends to form as a heterodimer vs. a homodimer.

Figure 44:
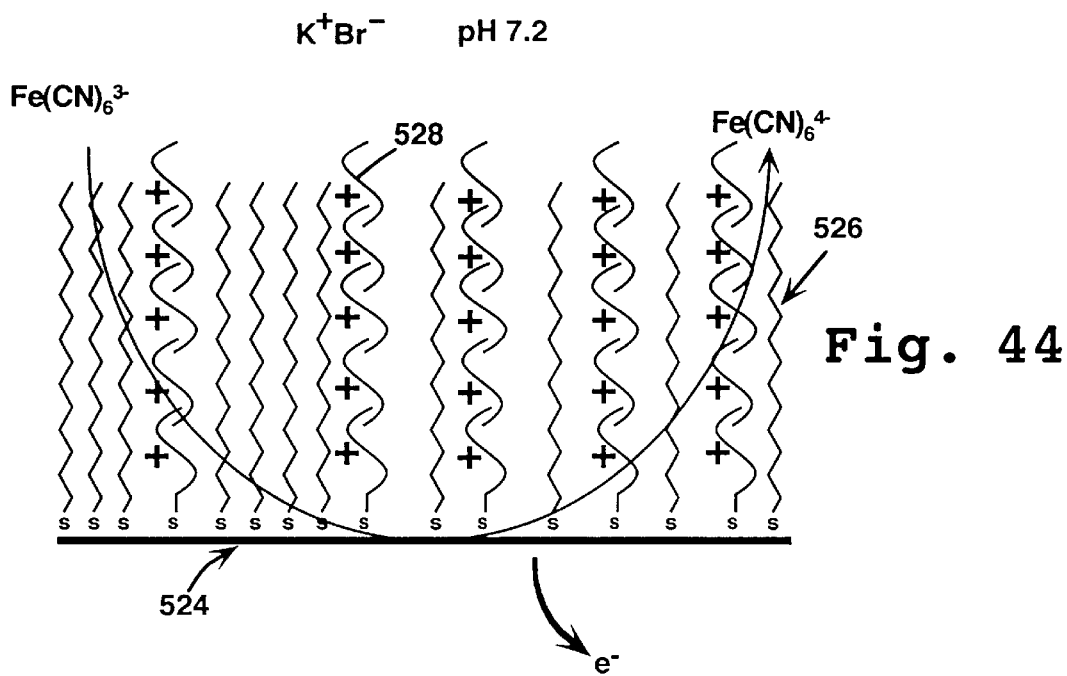
FIG. 44 illustrates the structure of an electrode monolayer having an embedded K-coil peptide subunit.

FIG. 44 shows a biosensor electrode 524 in which the hydrocarbon chain monolayer, indicated at 526 includes a K-coil peptide subunits, such as subunit 528, as described above. In the embodiment shown, each peptide subunit is coupled to the electrode surface via a tripeptide spacer, such as spacer 530 in subunit 528, which is itself attached to the electrode surface through a sulfhydryl linkage, as shown. The peptide, including the peptide spacer, is formed conventionally, e.g., by solid phase synthesis. The amount of peptide subunit in the monolayer is about 20 mole percent. The monolayer was formed according to the method described above with respect to FIG. 29. As indicated above, the peptide subunit may alternatively be coupled to the distal ends of a portion of the hydrocarbon chains in the monolayer, placing the subunit more on the monolayer surface. A hydrocarbon chain-peptide conjugate suitable for this application may be made, for example, by attaching an activated-end hydrocarbon chain to the terminal amino acid of the peptide, as the terminal step in solid phase synthesis.

Presumably because of the positive charge imparted to the monolayer by the K-coil subunits, the monolayer shows relatively high conductance to negatively charged redox species, such as $Fe(CN)_6^{3-}$, as evidenced by a relatively high oxidation or reduction current with the redox species.

Figure 46:
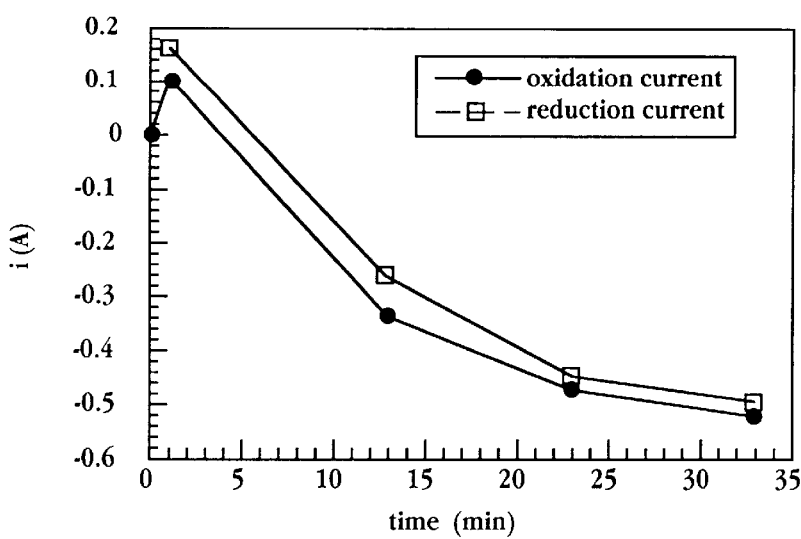
FIG. 46 shows the change in oxidation (solid circles) and reduction (open squares) current as a function of time after addition of E-coil peptide subunit to an electrode of the type illustrated in FIG. 44 containing an embedded K-coil peptide subunit.
Figure 55:
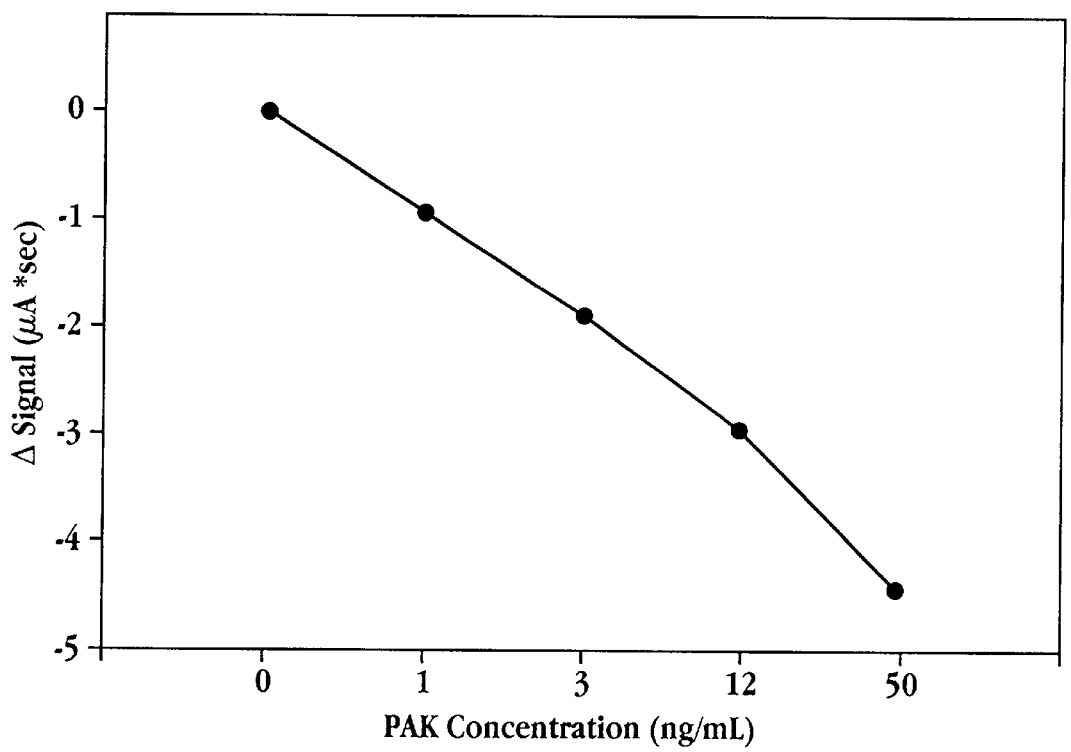
FIG. 55 is a plot showing change in biosensor signal, measured in nA*sec, as a function of PAK pilin peptide level in a competitve antibody binding assay.

FIG. 45 shows the same monolayer, but after addition of complementary, negatively charged E-coil subunits, such as indicated at 530. As shown, oppositely charged subunits pair to form charge-neutral heterodimers in the monolayer. This pairing is effective to reduce monolayer conductance substantially, as evidenced by the time-dependent fall in measured oxidation or reduction current in the presence of $Fe(CN)_6^{3-}$ ions (FIG. 46). A biosensor for determining PAK levels was constructed as described in Example 3 and demonstrates lower current at increased levels of PAK (FIG. 55). In Example 3, microtitre plates were coated with antibody to PAK protein receptor (PAK). Various levels of PAK were incubated in the wells with E-coil/PAK conjugate. At higher PAK concentration, more of the of the E-coil/PAK conjugate is free in solution due to competitive binding with the antibody. Originally the surface of the K/C16 chip is positively charged allowing a high flow of negatively charged redox probe. At higher amounts of conjugate, the E-coil binds with the K-coil and "neutralizes" the positive charge by forming charge-neutral heterodimers which led to a decrease in conductance.

Figure 47:
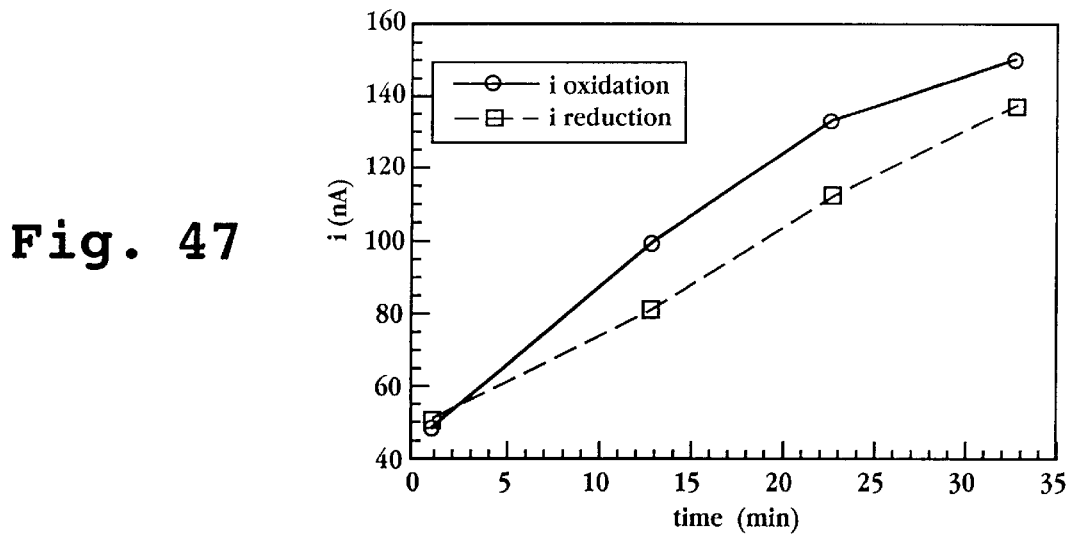
FIG. 47 shows changes in oxidation of $Fe(CN)_6^{3-/4-}$ (open circles) and reduction (open squares) as a function of time after addition of PAK peptide to an electrode containing di-saccharide ligands on a K-coil/E-coil lipid monolayer.
Figure 48:
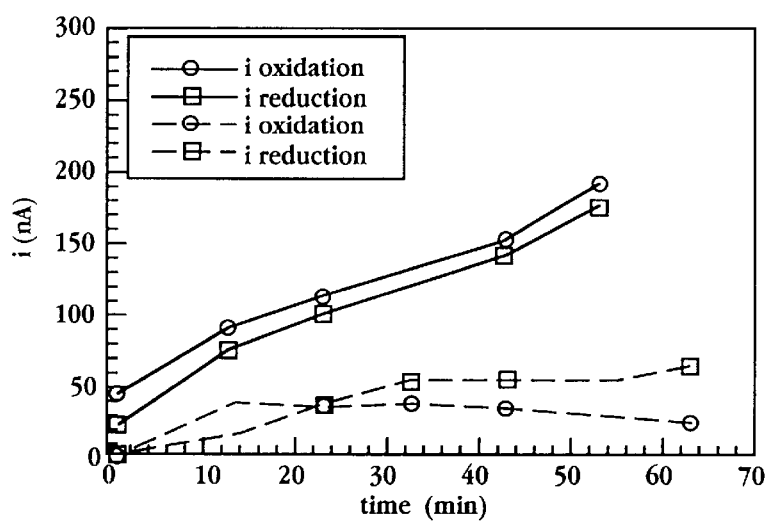
FIG. 48 shows changes in oxidation of $Fe(CN)_6^{3-/4-}$ (open circles) and reduction (open squares) as a function of time after addition of Verotoxin peptide to an electrode containing trisaccharide ligands on a K-coil/E-coil lipid monolayer.
Figure 53:
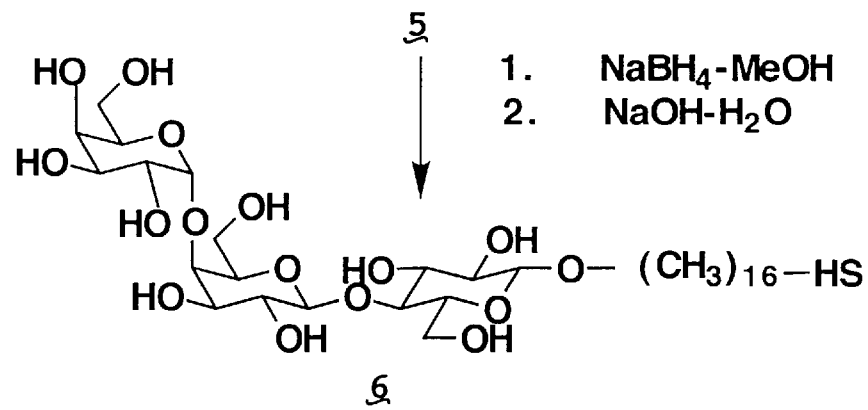
Figure 54:
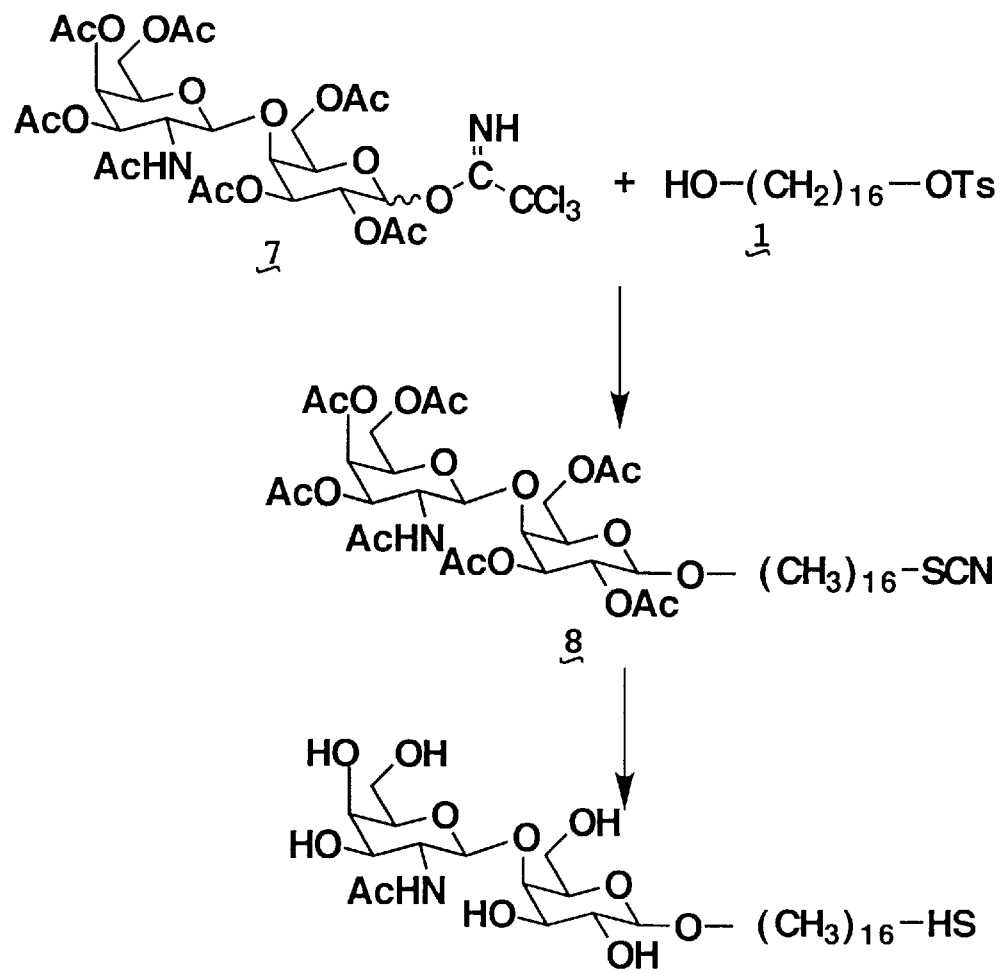
FIG. 54 shows a synthetic pathway used in producing a disaccharide-hydrocarbon conjugate employed in the monolayer shown in FIGS. 32 and 33.

In another embodiment of a biosensor for use in the present invention takes advantage of the pairing of subunits as shown in FIG. 45 (an in analogy to FIG. 29). In this embodiment, a second peptide subunit, e.g., the E-coil subunit, added to the monolayer is derivatized with an analyte-binding agent, producing a monolayer having charge-neutral heterodimers embedded therein (or attached to the monolayer surface), and an analyte-binding agent exposed on the monolayer surface. The resulting electrode is effective to measure analyte binding events in a biosensor operated in accordance with the invention. The operating characteristics of such a biosensor are illustrated in FIG. 46. The electrode in this biosensor includes (i) a monolayer with embedded K-coils covalently attached to the electrode surface, (ii) complementary E-coils forming heterodimers with the K-coils in the monolayer, and (iii) surface disaccharide analyte-binding agents of the type shown in FIG. 32 attached covalently to the E-coils and disposed therefore at the monolayer surface. As seen in FIG. 47, addition of the PAK protein analyte (see FIG. 33) produced an increase in both oxidation and reduction currents, with the current increase over time presumably reflecting additional binding events after analyte addition to the biosensor electrode. A similar biosensor having a trisaccharide, rather than disaccharide, analyte-binding agent attached to the E-coil subunit in the electrode monolayer was tested with the Verotoxin receptor described above with respect to FIGS. 35–37, with the results seen in FIG. 48. The solid lines in the figure show the increase in oxidation and reduction current observed, as a function of time, after addition of Verotoxin.

The following examples are intended to illustrate, but in no way limit the invention.

EXAMPLE 1

Synthesis of Receptors in a Form Suitable for Immobilization on a Gold Electrode Selective tosylation of 1,16-dihydroxyhexane provided the monotosylated alcohol 1 in 42% yield. Trisaccharide 2, obtained as described in the literature (Janson, et al., *J. Org. Chem.* 53:5629 (1988)), was converted into an anomeric mixture of trichloroacetamidates 3. Glycosylation of alcohol 1 with glycosyl donor 3 in $CH_2Cl_2$ in the presence of a catalytic amount of trimethylsilyl trifluoromethanesulfonate gave trisaccharide glycoside ω-tosylate 4, which was used in the next step without purification. The tosyloxy group of compound 4 was displaced by thiocyanate to provide the trisaccharide glycoside 5, terminated at the reducing end by spacer-arm containing the masked thiol function. Reduction of thiocyanate by the action of sodium borohydride (Olsen, R. K., and Snyder, H. R., *J. Org. Chem.* 30:184 (1965).) followed by saponification of acetate groups gave trisaccharide receptor 6.

The disaccharide imidate 7 was reacted with alcohol 1 in a similar fashion to that described for the trisaccharide 4. Synthesis of the disaccharide glycosyl donor 7 is not described here but follows established methods that are considered a general art. Nucleophilic substitution of the tosyloxy group by thiocyanate was carried out as described for preparation of 5 to give compound 8. Reduction of thiocyanate accompanies by deacetylation afforded synthetic disaccharide receptor 9.

A. 16-(p-Toluensulfonyloxy)hexadecanol (Structure 1)

To a solution of 1.1 g of 1,16-dihydroxyhexadecane in 10 ml of dry pyridine 0.8 g of tosyl chloride was added. After 2 h mixture was concentrated diluted with 20 ml of acetone, 5 g of $SiO_2$ was added and acetone was removed in vacuum. The solid was applied on $SiO_2$ and eluted with pentane-ethyl acetate (2:1) to yield 748 mg (42%) of C-101.

B. 2,3,4,6-tetra-O-acetyl-D-galactopyranasyl(α1→4)-6-O-acetyl-2,3-di-O-benzoyl-D-galactopyranosyl(β1→4)-2,3,6-tri-O-benzoyl-D-glucopyranosyl(β1→O)-(16-thiocyano) hexadecanol (Structure 5)

A mixture of 277 mg of imidate, 100 mg of C-101 and 0.5 g of mol. sieves (4A) was stirred for 1 h. Then 8 μL of TMSOTf was added. After 2 h 1 ml of EA was added, solid was removed by filtration. Filtrate was concentrated and dried in vacuum. A solution of the residue and 200 mg of KSCN in 6 ml of DMF was stirred at 80° C. for 2 hours. Mixture was concentrated, dissolved in 30 ml of CH2C12, washed with water and concentrated again. Chromatography of the residue on SiO2 with pentane-ethyl acetate (3:2) gave 225 ml (73%) of C-105.

C. D-Galactopyranosyl(α1→4)-D-galactopyranosyl(β1→4)-D-glucopyranosyl(β1→O)-(16-thio)hexadecanol (Structure 6)

To a solution of 60 mg of C-105 in 4 ml of dry MeOH~40 mg of NaBH4 was added Ar. After stirring for 2 h at 45° C. mixture was concentrated and dissolved under gentle reflux in a solution of 50 mg of NaOH in 10 ml of water. After stirring overnight at 45° C., the mixture was neutralized with cationite (H+-form) and applied on "Seppak" (C-18). The cartridge was washed with 20, 40, 50, 80, and 100% solution of MeOH in water. Fractions of 100% MeOH was concentrated to give 24.4 mg (81%) of C-106.

D. (16-thiocyano)hexadecanyl 4-O-(2-acetamido-3,4,6-tri-O-acetyl-2-D-galactopyranosyl)-2,3,6-O-acetyl-β-D-galactopyranoside C-108 (Structure 8)

Mixture of 100 mg of imidate 7, 68 mg of C-101 and 100 mg of mol. sieves (4A) in 5 ml of CH2C12 was stirred for 1 h. Then 5 μl of TMSOTf was added. After 2 h 1 ml of EA was added, solid was removed by filtration. Filtrate was concentrated and dried in vacuum. A solution of the residue and 70 mg of KSCN in 3 ml of DMF was stirred at 80° C. for 2 h. Mixture was concentrated, dissolved in 30 ml of CH2C12, was with water and concentrated again. Chromatography of the residue on SiO2 with pentane-ethyl acetate (2:1) gave 82 mg (70%) of C-108.

E. (16-thiohydroxy)hexadecanyl 4-O-(2-acetamido-2-deoxy-β-D-galactopyranosyl)-β-D-galactopyranoside (Structure 9)

A solution of 54.2 mg of 8 (C-108) and 40 mg of NaBH4 in 3 ml of dry MeOH was refluxed for 2 h then neutralized with Dowex (H+), concentrated and chromatographed on C-18 in $H_2O$ (50:50):100) to yield 19.7 mg (52%) of C-111.

EXAMPLE 2

Isolation of Verotoxin Receptor

Shiga-like (Vero) toxin I (SLT-I) was purified from *Escherichia coli* JM101 (pJB128) in a simple, one step procedure using CHROMOSORB-P containing covalently coupled synthetic analogs of the toxin's αGal(1,4)βGal (digalactoside) host cell receptors (SYNSORB-P1). Bacteria were grown in baffled Fernbach flasks at 37° C. in carbenicillin-(50 μg/ml) supplemented tryptic soy broth (TSB) containing SYNSORB-P1 (15 g/L) to bind toxin released from growing cells. Late log phase cultures were treated for 30 minutes at 37° C. with Polymyxin B sulfate (0.1 mg/mL) to release intracellular SLT-I and also allow this to bind to the SYNSORB-P1. Next, the SYNSORB-P1 was collected and washed thoroughly with 250 mM NaCl (pH 3.8) to remove cells and cellular debris. THe SLT-I was eluted from the washed SYNSORB-P1 using 50 mM Tris base (pH 10) containing 250 mM NaCl (TN) and concentrated using an Amicon ultrafiltration unit. The concentrated SLT-I was stable for weeks at 4° C. and could be frozen for extended periods of time without appreciable loss of activity. On average, 61% (n=10, SD mean=8, range 48% to 76%) of the SLT activity in the original Polymyxin-treated TSB cultures was recovered in the TN fraction eluted from the SYNSORB-P1. SDS-polyacrylamide gel electrophoretic analysis of the SLT-I preparation revealed two prominent Coomassie blue-stained bands. The molecular weight of these two bands was calculated to be 35,000 and 7,500, respectively. The 7.5 KDz band reacted in western immunoblots with SLT-I but not SLT-II B subunit-specific monoclonal antibody. Amino terminal microsequence analysis of both bands confirmed their identity as the A and B subunits of SLT-I. Average yield of SLT-I was 0.32 mg/L (n=8, SD mean=0.3, range 0.1 to 0.8) of TSB culture and its specific activity in the Vero cytotoxicity assay was 4.4 pg/mL/$CD_{50}$. The results demonstrate the utility of SYNSORB in the facile and rapid purification of carbohydrate binding toxins or lectins.

EXAMPLE 3

Immunoassay for PAK Protein

The *Pseudomonas aeruginosa* PAK pilin peptide has an amino acid sequence of KCTSDQDEQFIPKGCSK and was synthesized at the peptide synthesis facility of PENCE, University of Alberta, using the solid-phase peptide synthesis approach. The PAK-E coil peptide conjugate was recombinantly expressed and purified at Dr. Randall T. Irvin's laboratory. The mouse monoclonal antibody PK99H was also provided by Dr. Irvin. PK99H was classified as an IgG subclass 1 with $\mu$ light chains and prepared as a 295 $\mu$g protein/ml stock solution. The gold slides were purchased from Alberta Microelectronic Corp. Potassium ferricyanide was purchased from Aldrich.

The 96-well microtiter plate (Costar Corp.) was coated with the monoclonal antibody PK99H (295 ng/ml, 100 $\mu$l/well) in 10 mM carbonate buffer, pH 9.5. The plate was incubated at room temperature for 6 hr and was subsequently blocked with 3% BSA in PBS, pH 7.4, at 4° C. overnight. After blocking, the plate was washed three times with 0.05% BSA/PBS (Buffer A) and was ready for competitive binding study. A mixture of PAK-E coil conjugate (0.1 $\mu$g/ml) with various amount of PAK synthetic peptide (ranged from 0 to 0.2 $\mu$g/ml) was prepared and added into the wells containing the immobilized antibody in duplicate. The plate was allowed to incubate at 37° C. for 2 hours. The solution in each well was then transferred to microfuge tubes and was ready for biosensor analysis.

The presence of unbound PAK-E coil conjugate in the assay solution was detected electrochemically on a K coil/C16 coated gold electrode using ferricyanide as the electrochemical probe. The detection mechanism relies on the formation of coiled-coil heterodimer in the C16 monolayer that perturbs the permeability of the ferricyanide probe in generating the electric signal on the electrode surface.

The gold slides were washed 3 times with hot ethanol/chloroform solution (1:1 v/v) and ddH$_2$O before use. The K coil-SH (0.2 mM, 180 $\mu$l) was added dropwise onto the lower half of the gold surface. Then, incubation was taken place at room temperature for 2 hours and subsequently at 4° C. for 18 hours. After incubation, the slides were washed with ddH$_2$O and ethanol. The air-dried slides were then incubated with 0.5 mM of C16-SH in ethanol for 20 hours. After rinsing with ethanol and ddH$_2$O, the K coil/C16 coated gold slide was assembled to the Hewlett Packard (HP) flowcell as the working electrode. Electric current generated by the ferricyanide probe (1 mM in PBS) was monitored using the HP electrochemical detector and the HP 1100 HPLC system. Measurement was performed at 180 mV versus a Ag/AgCl reference electrode. Sample injection was carried out through a manual injector or an automated sampler. The injection volume was 20 $\mu$l in and the flow rate was 0.1 ml/min. Upon ferricyanide injection, a peak of current can be measured versus time. The peak area (in $\mu$A·sec) reflects the relative amount of ferricyanide probe that generates the electric signal on the electrode surface. Three measurements of ferricyanide injection were performed right after each sample injection. The average peak area of the last two ferricyanide runs were taken for data analysis.

The data are presented in FIG. 55 which shows the area under the peak ($\mu$A·sec) vs. concentration of PAK in the incubation.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

It is claimed:

1. A diagnostic card device for use in detecting or quantitating an analyte present in a liquid sample, comprising, a card substrate having formed therein a sample introduction region, a biosensor, and a sample-flow pathway communicating between said sample-introduction region and said biosensor, circuitry for generating an analyte-dependent electrical signal from the biosensor; and, a signal-responsive element for recording said signal, wherein said biosensor has a detection surface with surface-bound molecules of a first charged, coil-forming peptide for interacting with a second, oppositely charged coil-forming peptide to form a stable α-helical coiled-coil heterodimer, where the binding of the second peptide to the first peptide, to form said heterodimer, is effective to measurably alter a signal generated by the biosensor, and said sample-flow pathway contains (i) a conjugate of (ia) the second coil-forming peptide and (ib) the analyte or an analyte analog, and (ii) an analyte-binding agent immobilized within the pathway, wherein sample introduced in said sample introduction region is carried through the sample-flow pathway, where the analyte competes with said conjugate for binding to said analyte-binding agent, such that the presence of increasing amounts of analyte leads to increasing amounts of unbound conjugate which is then free to react with said first peptide in said biosensor to alter the signal generated by the biosensor in proportion to the amount of analyte present.

2. The device of claim 1, which further includes a background control biosensor and a control sample-flow pathway connecting the sample-introduction region to the background control biosensor, wherein said control sample-flow pathway does not include said conjugate.

3. The device of claim 1, which further includes a positive control biosensor not connected to the sample-introduction region and which includes a conjugate of (a) the second coil-forming peptide and (b) the analyte or an analyte analog in an amount sufficient to give a maximum biosensor response.

4. The device of claim 1, for use in detecting or quantitating a plurality of different analytes, which further includes, for each analyte, (i) a separate biosensor, and (ii) a separate sample-flow pathway connecting the sample-introduction region to each associated biosensor, where each sample-flow pathway includes (a) a conjugate of the second coil-forming peptide and one of the target analytes or analogs thereof, and (b) an associated analyte-binding agent.

5. The device of claim 4, wherein said sample introduction region comprises a single port communicating with each of the sample-flow pathways.

6. The device of claim 4, wherein said sample introduction region, sample-flow pathways and biosensors are microfabricated on said substrate.

7. The device of claim 1, wherein the sample-flow pathway includes a mixing zone containing the conjugate in releasable form, and a reaction zone containing the analyte-binding agent in immobilized form.

8. The device of claim 1, wherein the biosensor includes a conductive detection surface, a monolayer composed of hydrocarbon chains anchored at their proximal ends to the detection surface, and the first charged coil-forming peptide also anchored to said surface, where the binding of the second peptide to the first peptide, to form said heterodimer, is effective to measurably alter current flow across the monolayer mediated by a redox ion species in an aqueous solution in contact with the monolayer, relative to electron flow observed in the presence of the first peptide alone.

9. The device of claim 8, wherein said circuitry measures current flow across the detection surface, and output a signal related to measured current flow.

10. The device of claim 1, for use in detecting, in a sample, the presence or amount of an analyte, wherein the analyte binds with said analyte-binding agent to form an analyte/analyte-binding agent pair selected from the group consisting of antigen-antibody, hormone-receptor, drug-receptor, cell surface antigen-lectin, biotin-avidin, and complementary nucleic acid strands.

11. The device of claim 1, wherein said signal-responsive element comprises a liquid crystal display device.

12. The device of claim 11, wherein said liquid crystal display device comprises a linear color display device that responds to voltage level from said circuitry.

13. The device of claim 1, wherein said signal-responsive element comprises a magnetic recording medium effective to store a measured signal value from said circuitry.

14. The device of claim 13 for use with a magnetic reader device designed to read the measured signal value stored on said medium.

15. The device of claim 1, wherein said signal-responsive element is separable from portions of the card that are adapted to contact said sample, to provide a sample-free storage record of sample diagnostic results.

16. The device of claim 15 wherein said signal-responsive element comprises a magnetic recording medium effective to store a measured signal value from said circuitry.

* * * * *

SEQUENCE LISTING

```
<160> NUMBER OF SEQ ID NOS: 2

<210> SEQ ID NO 1
<211> LENGTH: 35
<212> TYPE: PRT
<213> ORGANISM: Artificial Sequence
<220> FEATURE:
<223> OTHER INFORMATION: peptide
<220> FEATURE:
<221> NAME/KEY: VARIANT
<222> LOCATION: (1)...(5)
<223> OTHER INFORMATION: EE peptide

<400> SEQUENCE: 1

Glu Val Glu Ala Leu Gln Lys Glu Val Ser Ala Leu Glu Lys Glu Val
 1               5                  10                  15

Ser Ala Leu Glu Cys Glu Val Ser Ala Leu Glu Lys Glu Val Glu Ala
            20                  25                  30

Leu Gln Lys
        35

<210> SEQ ID NO 2
<211> LENGTH: 35
<212> TYPE: PRT
<213> ORGANISM: Artificial Sequence
<220> FEATURE:
<223> OTHER INFORMATION: peptide
<220> FEATURE:
```

-continued

```
<221> NAME/KEY: VARIANT
<222> LOCATION: (1)...(35)
<223> OTHER INFORMATION: KK peptide

<400> SEQUENCE: 2

Lys Val Glu Ala Leu Lys Lys Val Ser Ala Leu Lys Glu Lys Val
 1               5                  10                  15

Ser Ala Leu Lys Cys Lys Val Ser Ala Leu Lys Glu Lys Val Glu Ala
            20                  25                  30

Leu Lys Lys
        35
```